United States Patent
Lee et al.

(10) Patent No.: US 11,007,251 B2
(45) Date of Patent: May 18, 2021

(54) AMELIORATING SYSTEMIC SCLEROSIS WITH DEATH RECEPTOR AGONISTS

(71) Applicant: The Johns Hopkins University, Baltimore, MD (US)

(72) Inventors: Seulki Lee, Elkridge, MD (US); Martin G. Pomper, Baltimore, MD (US); Jong-Sung Park, Elkridge, MD (US); Yumin Oh, Elkridge, MD (US); Magdalena Scully, Columbia, MD (US); Maureen Horton, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 180 days.

(21) Appl. No.: 16/063,592

(22) PCT Filed: Dec. 16, 2016

(86) PCT No.: PCT/US2016/067145
§ 371 (c)(1),
(2) Date: Jun. 18, 2018

(87) PCT Pub. No.: WO2017/106627
PCT Pub. Date: Jun. 22, 2017

(65) Prior Publication Data
US 2019/0000924 A1    Jan. 3, 2019

Related U.S. Application Data

(60) Provisional application No. 62/268,637, filed on Dec. 17, 2015.

(51) Int. Cl.
*A61K 38/19* (2006.01)
*A61K 31/25* (2006.01)
(Continued)

(52) U.S. Cl.
CPC .......... *A61K 38/191* (2013.01); *A61K 38/177* (2013.01); *A61K 39/39541* (2013.01);
(Continued)

(58) Field of Classification Search
None
See application file for complete search history.

(56) References Cited

U.S. PATENT DOCUMENTS

| | | | |
|---|---|---|---|
| 4,816,397 A | 3/1989 | Boss | |
| 4,816,567 A | 3/1989 | Cabilly | |

(Continued)

FOREIGN PATENT DOCUMENTS

| | | |
|---|---|---|
| GB | 2188638 | 10/1987 |
| GB | 2209757 | 5/1989 |

(Continued)

OTHER PUBLICATIONS

Golan-Gerstl et al., Epithelial cell apoptosisi by Fas ligand-positive myofibroblats in lung fibrosis, Am. J. Respir. Cel. Mol. Biol. 36: 270-275, 2007.*

(Continued)

*Primary Examiner* — Claire Kaufman
(74) *Attorney, Agent, or Firm* — Pabst Patent Group LLP

(57) ABSTRACT

The present disclosure relates to methods and compositions for treating and/or preventing autoimmune fibrosis, such as systemic sclerosis (SSc; scleroderma). The method includes administering to a subject in need thereof an effective amount of a death receptor agonist. Suitable death receptor agonists include tumor necrosis factor (TNF)-related apoptosis inducing ligand (TRAIL), agonistic death receptor antibodies, and variants, analogues, or derivatives thereof. The administration of the death receptor agonist blocks (Continued)

fibroblast or profibrogenic cell activation, and/or reduces or depletes myofibroblasts, thereby reducing or preventing systemic sclerosis.

24 Claims, 7 Drawing Sheets

Specification includes a Sequence Listing.

(51) Int. Cl.
| | |
|---|---|
| A61K 39/395 | (2006.01) |
| C07K 16/28 | (2006.01) |
| A61K 47/60 | (2017.01) |
| A61K 38/17 | (2006.01) |
| A61K 39/00 | (2006.01) |
| A61P 37/06 | (2006.01) |

(52) U.S. Cl.
CPC .......... *A61K 47/60* (2017.08); *C07K 16/2878* (2013.01); *A61K 2039/505* (2013.01); *A61P 37/06* (2018.01); *C07K 2317/21* (2013.01); *C07K 2317/75* (2013.01)

(56) References Cited

U.S. PATENT DOCUMENTS

| | | | |
|---|---|---|---|
| 5,565,332 A | 10/1996 | Hoogenboom | |
| 5,624,821 A | 4/1997 | Winter | |
| 5,721,367 A | 2/1998 | Kay | |
| 5,763,223 A | 6/1998 | Wiley | |
| 5,837,243 A | 11/1998 | Deo | |
| 5,939,598 A | 8/1999 | Kucherlapati | |
| 6,072,047 A | 6/2000 | Rauch | |
| 6,130,364 A | 10/2000 | Jakobovits | |
| 6,180,377 B1 | 1/2001 | Morgan | |
| 6,194,551 B1 | 2/2001 | Idusogie | |
| 6,329,148 B1 | 12/2001 | Rosen | |
| 6,331,415 B1 | 12/2001 | Cabilly | |
| 6,908,963 B2 | 6/2005 | Roberts | |
| 7,060,272 B2 | 6/2006 | Ni | |
| 7,160,924 B2 | 1/2007 | Kinstler | |
| 7,186,699 B2 | 3/2007 | Harding | |
| 7,368,295 B2 | 5/2008 | Tovar | |
| 7,521,056 B2 | 4/2009 | Chang | |
| 7,534,866 B2 | 5/2009 | Chang | |
| 7,550,143 B2 | 6/2009 | Chang | |
| 7,615,233 B2 | 11/2009 | Yano | |
| 7,795,404 B1 | 9/2010 | Lin | |
| 7,897,730 B2 | 3/2011 | Yu | |
| 7,906,118 B2 | 3/2011 | Chang | |
| 7,994,281 B2 | 8/2011 | Tur | |
| 8,003,111 B2 | 8/2011 | Chang | |
| 8,008,261 B2 | 8/2011 | Badley | |
| 8,029,783 B2 | 10/2011 | Adams | |
| 8,034,352 B2 | 10/2011 | Chang | |
| 8,075,916 B2 | 12/2011 | Song | |
| 8,143,380 B2 | 3/2012 | Walker | |
| 8,158,129 B2 | 4/2012 | Chang | |
| 8,198,033 B2 | 6/2012 | Austin | |
| 8,282,934 B2 | 10/2012 | Chang | |
| 8,287,888 B2 | 10/2012 | Song | |
| 8,435,540 B2 | 5/2013 | Chang | |
| 8,440,787 B2 | 5/2013 | McManus | |
| 8,461,311 B2 | 6/2013 | Hawkins | |
| 8,568,721 B2 | 10/2013 | Radin | |
| 8,586,020 B2 | 11/2013 | Song | |
| 8,597,659 B2 | 12/2013 | Chang | |
| 8,628,801 B2 | 1/2014 | Garreta | |
| 8,673,923 B2 | 3/2014 | El-Deiry | |
| 8,709,409 B2 | 4/2014 | Okuda | |
| 8,986,684 B2 | 3/2015 | Wang | |
| 9,017,726 B2 | 4/2015 | Song | |
| 9,102,735 B2 | 8/2015 | Govindan | |
| 9,150,846 B2 | 10/2015 | Jefferies | |
| 9,901,620 B2 * | 2/2018 | Lee | C07K 14/70578 |
| 2002/0058029 A1 | 5/2002 | Hanna | |
| 2002/0061525 A1 | 5/2002 | Yelin | |
| 2002/0169123 A1 | 11/2002 | El-Deiry | |
| 2004/0005314 A1 | 1/2004 | Escandon | |
| 2004/0146896 A1 | 7/2004 | Rong | |
| 2004/0146968 A1 | 7/2004 | Chung | |
| 2004/0186051 A1 | 9/2004 | Kelley | |
| 2005/0203142 A1 | 9/2005 | Zeldis | |
| 2006/0141561 A1 | 6/2006 | Kelley | |
| 2006/0188498 A1 | 8/2006 | Ashkenazi | |
| 2006/0228352 A1 | 10/2006 | Schoenberger | |
| 2007/0066800 A1 | 3/2007 | Sidhu | |
| 2008/0044421 A1 | 2/2008 | Ashkenazi | |
| 2008/0199423 A1 | 8/2008 | Godowski | |
| 2008/0305038 A1 | 12/2008 | Rosenecker | |
| 2009/0022683 A1 | 1/2009 | Song | |
| 2009/0081157 A1 | 3/2009 | Kornbluth | |
| 2009/0203599 A1 | 8/2009 | Lee | |
| 2009/0203671 A1 | 8/2009 | Glaser | |
| 2009/0258017 A1 | 10/2009 | Callahan | |
| 2009/0324616 A1 | 12/2009 | Stassi | |
| 2009/0325867 A1 | 12/2009 | Cohen | |
| 2010/0068302 A1 | 3/2010 | Ramirez De Molina | |
| 2010/0105620 A1 | 4/2010 | Bowdish | |
| 2010/0209490 A1 | 8/2010 | Morita | |
| 2010/0239554 A1 | 9/2010 | Schellenberger | |
| 2011/0020273 A1 | 1/2011 | Chang | |
| 2011/0038855 A1 | 2/2011 | Schoenberger | |
| 2011/0104103 A1 | 5/2011 | Heetebrij | |
| 2011/0165265 A1 | 7/2011 | Samali | |
| 2011/0200552 A1 | 8/2011 | Rodrigues Dos Reis | |
| 2011/0262455 A1 | 10/2011 | Samali | |
| 2012/0021995 A1 | 1/2012 | Bowdish | |
| 2013/0079280 A1 | 3/2013 | Baca | |
| 2013/0101553 A1 | 4/2013 | Kisseleva | |
| 2013/0150566 A1 | 6/2013 | Hua | |
| 2013/0178416 A1 | 7/2013 | Chilkoti | |
| 2013/0195884 A1 | 8/2013 | Boutros | |
| 2013/0217091 A1 | 8/2013 | Chang | |
| 2014/0004081 A1 | 1/2014 | Cobbold | |
| 2014/0004120 A1 | 1/2014 | Ohtsuka | |
| 2014/0079722 A1 | 3/2014 | Prudent | |
| 2014/0086907 A1 | 3/2014 | Shah | |
| 2014/0096274 A1 | 4/2014 | Quax | |
| 2014/0105898 A1 | 4/2014 | Thomas | |
| 2014/0134647 A1 | 5/2014 | Benedict | |
| 2014/0135377 A1 | 5/2014 | Westermarck | |
| 2014/0161766 A1 | 6/2014 | Chang | |
| 2014/0178398 A1 | 6/2014 | Ashkenazi | |
| 2014/0206843 A1 | 7/2014 | Zhou | |
| 2015/0038511 A1 | 2/2015 | Schafer | |
| 2015/0056159 A1 | 2/2015 | Kontermann | |
| 2015/0056204 A1 | 2/2015 | Holland | |
| 2015/0174269 A1 | 6/2015 | Govindan | |
| 2015/0183875 A1 | 7/2015 | Cobbold | |
| 2015/0197730 A1 | 7/2015 | Shah | |
| 2015/0204877 A1 | 7/2015 | Westermarck | |
| 2015/0218282 A1 | 8/2015 | Shah | |
| 2015/0250896 A1 | 9/2015 | Zhao | |
| 2015/0259397 A1 | 9/2015 | Lee | |
| 2015/0284416 A1 | 10/2015 | Zhao | |
| 2015/0301058 A1 | 10/2015 | Schettini | |
| 2016/0022776 A1 | 1/2016 | Lee | |

FOREIGN PATENT DOCUMENTS

| | | |
|---|---|---|
| KR | 1020020010363 | 2/2002 |
| WO | 98031383 | 7/1998 |
| WO | 9900423 | 1/1999 |
| WO | 99058572 | 11/1999 |
| WO | 2000069911 | 11/2000 |
| WO | 0122987 | 4/2001 |
| WO | 2004001009 | 12/2003 |
| WO | 2004022004 | 3/2004 |
| WO | 2006028939 | 3/2006 |
| WO | 2006042848 | 4/2006 |
| WO | 2006107617 | 10/2006 |
| WO | 2006107786 | 10/2006 |

(56) References Cited

FOREIGN PATENT DOCUMENTS

| WO | 2007046893 | 4/2007 |
|---|---|---|
| WO | 2007075534 | 7/2007 |
| WO | 2007102690 | 9/2007 |
| WO | 2007145457 | 12/2007 |
| WO | 2008120832 | 10/2008 |
| WO | 2008130066 | 10/2008 |
| WO | 2009058379 | 5/2009 |
| WO | 2009126558 | 10/2009 |
| WO | 2009140469 | 11/2009 |
| WO | 2010093395 | 8/2010 |
| WO | 2010121559 | 10/2010 |
| WO | 2011025904 | 3/2011 |
| WO | 11079293 | 6/2011 |
| WO | 2011106707 | 9/2011 |
| WO | 2014044768 | 3/2014 |
| WO | 2014121093 | 8/2014 |
| WO | 2014126537 | 8/2014 |
| WO | 2015010615 | 1/2015 |
| WO | 2015028850 | 3/2015 |
| WO | 2015037000 | 3/2015 |
| WO | 15092756 | 6/2015 |
| WO | 2015127685 | 9/2015 |
| WO | 2015164217 | 10/2015 |

OTHER PUBLICATIONS

Wegner et al.,Edar is a downstream target of beta-catenin and drives collagen accumulation in the mouse prostate, Biology Open, b io037945. doi: 10.1242/bio.037945, 8:1-6, 2019.*

Shih et al., Inhibition of a novel fibrogenic factor TIIa reverses established colonic fibrosisNature, 7(6):1492-1503, Nov. 2014.*

Ley et al., How mouse macrophages sense what is going on, [Retrieved online: <URL:https://doi.org/10.3389/fimmu.2016. 00204>, on Apr. 24, 2020] Frontiers Immunol. 7:204 (1-17), Jun. 2016.*

Kendall et al., p75 neurotrophin receptor signaling regulates hepatic myofibroblast proliferation and apoptosis in recovery from rodent liver fibrosis, Hepatol. 49:901-910, 2009.*

Tarrats et al., Critical role of tumor necrosis factor receptor 1, but not 2, in hepatic stellate cell proliferation, extracellular matrix remodeling, and liver fibrogenesis, Hepatol. 54:319-327, 2011.*

Fox et al., Tumor necrosis factor-related apoptosis-inducing ligand (TRAIL) receptor-1 and receptor-2 agonists for cancer therapy , Exp. Opin. Biol. Ther. 10, 1-18, 2010.*

Yurovsky, V.V., Cross-talk between TRAIL and TGF-β in regulation of collagen production in scleroderma lung disease, Arthritis Res. Ther. 6:26, 2004 (doi.org/10.1186/ar1068) . . . .*

Yurovsky, V.V., Effect of TRAIL on collagen production by human lung fibroblasts, FASEB J. 15(5): A1045, Mar. 8, 2001.*

LoRusso et al., First-in-human study of AMG 655, a pro-apoptotic TRAIL receptor-2 agonist, in adult patients with advanced solid tumors , J. Clin. Oncol. ASCO Meeting Abstracts. 25(18 suppl):3534, Jun. 20, 2007.*

Saleh et al., A phase I study of CS-1008 (humanized monoclonal antibody targeting death receptor 5 or DR5), administered weekly to patients with advanced solid tumors or lymphomas, J. Clin. Oncol., 26(15 suppl):3537, May 20, 2008.*

Darby et al., Fibroblasts and myofibroblasts in wound healing, Clin. Cosmetic Invest. Dermatol. 47:301-311, Nov. 2014.*

Akram, et al., "Alveolar epithelial cells in idiopathic pulmonary fibrosis display upregulation of TRAIL, DR4 and DR5 expression with simultaneous preferential over-expression of pro-apoptotic marker p53", Int. J. Clin. Exp. Pathol., 7(2):552-564 (2014).

Al-Sabah, et al., "A model for receptor—peptide binding at the glucagon-like peptide-1 (GLP-1) receptor through the analysis of truncated ligands and receptors", Br J Pharma, 140:339-46 (2003).

Alconcel et al., "FDA-approved poly(ethylene glycol)-protein conjugate drugs", Polymer Chemistry, 2(7):1442-48 (2011).

Amiram, et al., "Injectable protease-operated depots of glucagon-like peptide-1 provide extended and tunable glucose control", PNAS, 110(8); 2792-7 (2013).

Anel, et al., "Apo2L/TRAIL and immune regulation", Front Biosci., 12:2074-84 (2007).

Ashkenazi et al., "Ligand-based targeting of apoptosis in cancer: the potential of recombinant human apoptosis ligand 2/Tumor necrosis factor-related apoptosis-inducing ligand (rhApo2L/TRAIL)", J Clin Oncol, 26(21):3621-30 (2008).

Audo, et al., "The two directions of TNF-related apoptosis-inducing ligand in rheumatoid arthritis", Cytokine, 63(2):81-90 (2013).

Bajaj, et al., "Conatumumab: a novel monoclonal antibody against death receptor 5 for the treatment of advanced malignancies in adults", Expert Opinion on Biological Therapy, 11(11):1519-1524 (2011).

Bataller, et al., "Hepatic stellate cells as target for treatment of liver fibrosis", Semin Liver Dis, 21(03):437-52 (2001).

Bataller, et al., "Liver fibrosis", Clin. Invest., 115(2):209-18 (2005).

Beljaars, et al., "Successful targeting to rat hepatic stellate cells using albumin modified with cyclic peptides that recognize the collagen type VI receptor", J Biol Chem., 275:12743-51 (2000).

Benedict, et al., "TRAIL: not just for tumors anymore", J. Exp. Med., 209(11):1903-6 (2012).

Bertola, et al., "Mouse model of chronic and binge ethanol feeding (the NIAAA model)", Nat Protoc., 8(3):627-37 (2013).

Bhattacharyya, et al., "Understanding fibrosis in systemic sclerosis: shifting paradigms, emerging opportunities", Nat Rev Rheumatol., 8(1):42-54 (2012).

Boerner, et al., "Production of antigen-specific human monoclonal antibodies from in vitro-primed human splenocytes", J. Immunol., 147(1):86-95 (1991).

Byeon, et al., "Human serum albumin-TRAIL conjugate for the treatment of rheumatoid arthritis", Bioconjug Chem., 25(12):2212-21 (2014).

Chae, et al., "Improved antitumor activity and tumor targeting of NH(2)-terminal-specific PEGylated tumor necrosis factor-related apoptosis-inducing ligand", Molecular cancer therapeutics 9(6):1719-29 (2010).

Cuello, et al., "Synergistic induction of apoptosis by the combination of trail and chemotherapy in chemoresistant ovarian cancer cells", Gynecol Oncol., 81(3):380-90 (2001).

Definition of Dimer, Thefreedictionary.com, 2 pages, accessed Dec. 8, 2014.

Definition of Trimer, thefreedictionary.com, 2 pages, accessed Dec. 8, 2014.

Deng, et al., "Chronic alcohol consumption accelerates fibrosis in response to cerulein-induced pancreatitis in rats", Am J Pathol,. 166(1):93-106 (2005).

Erkan, et al., "StellaTUM: current consensus and discussion on pancreatic stellate cell research", Gut. 61(2):172-8 (2012).

Fee, et al., "Size comparison between proteins PEGylated with branched and linear poly(ethylene glycol) molecules", Biotechnol Bioeng., 98(4):725-3 (2007).

Friedman, "Evolving challenges in hepatic fibrosis", Nat Rev Gastroenterol Hepatol. 7(8):425-36 (2010).

Friedman, "Fibrogenic cell reversion underlies fibrosis regression in liver", PNAS, 109(24):9230-1 (2012).

Gieffers, "APG350 induces superior clustering of TRAIL receptors and shows therapeutic antitumor efficacy independent of cross-linking via Fcγ receptors", Mol Cancer Ther, 12(12):2735-¬47 (2013).

Gong et al., "Site-specific PEGylation of exenatide analogues markedly improved their glucoregulatory activity", Br J Pharmacol, 163(2):399-412 (2011).

Harith, et al., "On the TRAIL of obesity and diabetes", Trends Endocrinol Metabol., 24(11):578-587 (2013).

Hasel, et al., "In chronic pancreatitis, widespread emergence of TRAIL receptors in epithelia coincides with neoexpression of TRAIL by pancreatic stellate cells of early fibrotic areas", Laboratory Investigation, 83(6):825-836 (2003).

Herbst, et al., "Phase I dose-escalation study of recombinant human Apo2L/TRAIL, a dual proapoptotic receptor agonist, in patients with advanced cancer", J. Clin. Oncol., 28(17):2839-46 (2010).

(56) References Cited

OTHER PUBLICATIONS

Ho, et al., "Fibrosis—a lethal component of systemic sclerosis", Nat Rev Rheumatol, 10(7): 390-402 (2014).
International Search Report and Written Opinion for PCT/US2015/020015 dated Jul. 8, 2015.
International Search Report for corresponding PCT application PCT/US2015/026513 dated Jun. 7, 2015.
International Search Report for PCT/US2016/067145 dated Mar. 27, 2017.
International Search Report for PCT/US2017/026617 dated Jul. 4, 2017.
Iredale, et al., "Mechanisms of spontaneous resolution of rat liver fibrosis. Hepatic stellate cell apoptosis and reduced hepatic expression of metalloproteinase inhibitors", J Clin Invest, 102(3):538-49 (1998).
Jeffrey, et al., "1,25-Dihydroxyvitamin D3 and IL-2 combine to inhibit T cell production of inflammatory cytokines and promote development of regulatory T cells expressing CTLA-4 and FoxP3", The Journal of Immunology, 183:5458-5467 (2009).
Jin, et al, "Effect of tumor necrosis factor-related apoptosis-inducing ligand on the reduction of joint inflammation in experimental rheumatoid arthritis", J. Pharmacol. Exp. Ther. 332(3):858-65 (2010).
Jo, et al., "Apoptosis induced in normal human hepatocytes by tumor necrosis factor-related apoptosis-inducing ligand", Nature Med., 6(5):564-7 (2000).
Kelley, et al., "Preclinical Studies to Predict the Disposition of Apo2L/Tumor Necrosis Factor-Related Apoptosis-Inducing Ligand in Humans: Characterization of in Vivo Efficacy, Pharmacokinetics, and Safety", J Pharmacol Exp Ther, 299(1):31-8 (2001).
Kim, et al., "A sulfate polysaccharide/TNF-related apoptosis-inducing ligand (TRAIL) complex for the long-term delivery of TRAIL in poly(lactic-co-glycolic acid) (PLGA) microspheres", J Pharma Pharmacol, 65(1):11-21 (2013).
Kim, et al., "Bioimaging for targeted delivery of hyaluronic Acid derivatives to the livers in cirrhotic mice using quantum dots", ACS Nano, 4(6):3005-14 (2010b).
Kim, et al., "Ionic complex systems based on hyaluronic acid and PEGylated TNF-related apoptosis-inducing ligand for treatment of rheumatoid arthritis", Biomaterials, 31(34):9057-64 (2010a).
Kim, et al., PEGylated TNF-related apoptosis-inducing ligand (TRAIL) analogues: pharmacokinetics and antitumor effects Bioconjugate Chem., 22 (8):1631-7 (2011a).
Kim, et al., "PEGylated TNF-related apoptosis-inducing ligand (TRAIL)-loaded sustained release PLGA microspheres for enhanced stability and antitumor activity", J Control Rel., 150(1):63-¬9 (2011b).
Kim, et al., "Preparation and characterization of Apo2L/TNF-related apoptosis-inducing ligand-loaded human serum albumin nanoparticles with improved stability and tumor distribution", J Pharm Sci, 100(2):482-91 (2011c).
Kim, et al., "Site-specific PEGylated Exendin-4 modified with a high molecular weight trimeric PEG reduces steric hindrance and increases type 2 antidiabetic therapeutic effects", Bioconjug Chem., 23(11):2214-20 (2012).
Kim, et al., "The secretable form of trimeric TRAIL, a potent inducer of apoptosis", BBRC, 321:930-5 (2004).
Kinstler, et al., "Mono-N-terminal poly(ethylene glycol)-protein conjugates", Adv. Drug Delivery Rev., 54:477-485 (2002).
Lakner, et al., "Inhibitory effects of microRNA 19b in hepatic stellate cell-mediated fibrogenesis", Hepatology, 56(1):300-10 (2012).
Lamhamedi-Cherradi, et al., "Defective thymocyte apoptosis and accelerated autoimmune diseases in TRAIL-/-mice", Nat Immunol., 4(3):255-60 (2003).
Lee, et al., "1004 Treatment with PEGylated TNF-related apoptosis-inducing ligand (TRAIL) induces apoptosis of human rheumatoid arthritis (RA) fibroblast-like synoviocytes (FLS) and suppresses arthritis in murine collagen-induced arthritis", Arthritis and Rheumatism, 72nd Annual scientific meeting of the American college of Rheumatology/43rd annual scientific meeting, Wiley San Francisco, CA, 58(9): Suppl S:s539 (2008).
Lee, et al., "A novel-trail-based therapy for chronic pancreatitis", Gastroenterology, 152(5):XP029979046 (2017). Abstract.
Lemke, et al., "Getting TRAIL back on track for cancer therapy", Cell Death Diff, 21(9):1350-64 (2014).
Li, et al., "Anti-DR5 mAb ameliorate adjuvant arthritis rats through inducing synovial cells apoptosis", Exp biology Med, 234(12):1468-76 (2009).
Liao, et al., "Trail reduced joint inflammation, osteoclast activation and and loss in experimental arthritis", Allergy, 68(98):67 (2013).
Liu, et al., "CII-DC-AdTRAIL cell gene therapy inhibits infiltration of CII-reactive T cells and CII-induced arthritis", J Clin Invest., 112(9):1332-41 (2003).
Louis, et al., "Interleukin-10 controls neutrophilic infiltration, hepatocyte proliferation, and liver fibrosis induced by carbon tetrachloride in mic", Hepatology, 28:1607-15 (1998).
Ma, et al., "TNF inhibitor therapy for rheumatoid arthritis (Review)", Biomed Reports, 1(2):177-84 (2012).
MacKay and Ambrose, "The TNF family members BAFF and APRIL: the growing complexity", Cytokine Growth Factor Rev, 14(3-4):311-24 (2003).
MacKay and Kalled, "TNF ligands and receptors in autoimmunity: an update", Curr Opin Immunol, 14: 783-90 (2002).
Martinez-Lostao, et al., "Liposome-bound APO2L/TRAIL is an effective treatment in a rabbit model of rheumatoid arthritis", Arthritis Rheum., 62(8):2272-82 (2010).
Mayo Clinic, "Diabetes", www.mayoclinic.org/diseases-conditions/diabetes/in-depth/diabetes-symthoms/art, 2 pages, accessed Dec. 19, 2014.
McInnes, et al., "Cytokines in the pathogenesis of rheumatoid arthritis", Nature Rev Immunol., 7(6):429-42 (2007).
Miranda-Carus, et al., "Rheumatoid arthritis synovial fluid fibroblasts express TRAIL-R2 (DR5) that is functionally active", Arthritis Rheum., 50(9):2786-93 (2004).
Molineux, "The design and development of pegfilgrastim (PEG-rmetHuG-CSF, Neulasta)", Cur Pharm Des, 10(11):1235-44 (2004).
Nikpour, et al., "Mortality in systemic sclerosis: lessons learned from population-based and observational cohort studies", Curr Opin Rheumatol, 26(2):131-7 (2014).
Omary, et al., "The pancreatic stellate cell: a star on the rise in pancreatic diseases", J Clin Invest, 117(1):50-59 (2007).
Park, et al., "Down-regulation of Fox0-dependent c-FLIP expression mediates Trail-induced apoptosis in activated hepatic stellate cells", Cell Signal., 21(10):1495-503 (2009).
Pavet, et al., "Multivalent DR5 peptides activate the TRAIL death pathway and exert tumoricidal activity", Cancer Res., 70:1101-10, (2010).
Pinzani, "Pancreatic stellate cells: new kids become mature", Gut, 55(1):12-14 (2006).
Poelstra, et al., "Drug targeting to the diseased liver", J. Control Release, 161(2):188-97 (2012).
Radaeva, et al., "Natural killer cells ameliorate liver fibrosis by killing activated stellate cells in NKG2D-dependent and tumor necrosis factor-related apoptosis-inducing ligand-dependent manners", Gastroenterology, 130(2):435-52 (2006).
Reichling and Levine,"Critical role of nociceptor plasticity in chronic pain", Trends Neurosci, 32(12):611-8 (2009).
Rieux-Laucat, et al, "Cell-death signaling and human disease", Curr. Opin. Immunol., 15:325-31 (2003).
Shibata, et al., "Functionalization of tumor necrosis factor-a using phase display technique and PEGylation improves its antitumor therapeutic window", Clin Cancer Res., 10:8293-300 (2004).
Song, et al., "Tumor necrosis factor-related apoptosis-inducing ligand (TRAIL) is an inhibitor of autoimmune inflammation and cell cycle progression", J Exp Med., 191(7):1095-104 (2000).
Strejan, et al, "Suppression of chronic-relapsing experimental allergic encephalomyelitis in strain-13 guinea pigs by administration of liposome-associated myelin basic protein", J. Neuroimmunol, 7(1):27-41 (1984).

(56) References Cited

OTHER PUBLICATIONS

Taimr, "Activated stellate cells express the TRAIL receptor-2/death receptor-5 and undergo TRAIL-mediated apoptosis", Hepathology, 37(1):89-95 (2003).
TNFSF10, symbol report, http://www.genenames.org/data/hgnc_data.php?hgnc_id=11925, 1 page, downloaded Mar. 8, 2011.
Tur, "DR4-selective tumor necrosis factor-related apoptosis-inducing ligand (TRAIL) variants obtained by structure-based design", J. Biol Chem, 283(29):20560-8 (2008).
Van Der Sloot, "Designed tumor necrosis factor-related apoptosis-inducing ligand variants initiating apoptosis exclusively via the DR5 receptor", PNAS, 103(23):8634-9 (2006).
Varga, et al., "Systemic sclerosis: a prototypic multisystem fibrotic disorder", J. Clin Invest, 117(3):557-67 (2007).
Wahl, "Increased apoptosis induction in hepatocellular carcinoma by a novel tumor-targeted TRAIL fusion protein combined with bortezomib", Hepatology, 57(2):625-36 (2013).
Walczak, et al., "Tumoricidal activity of tumor necrosis factor-related apoptosis-inducing ligand in vivo", Nature Med., 5(2):157-63 (1999).
Wang, et al., "Small-molecule activation of the TRAIL receptor DR5 in human cancer cells", Nature Chemical Biology, 9:84-9 (2013).
Wu, et al., "Regression of human mammary adenocarcinoma by systemic administration of a recombinant gene encoding the hFlex-TRAIL fusion protein", Mole Therapy, 3(3):368-74 (2001).
Wu, et al., "TRAIL and chemotherapeutic drugs in cancer therapy", Vitam Horm., 67:365-83 (2004).
Xiang, et al., "Tissue distribution, stability, and pharmacokinetics of APO2 ligand/tumor necrosis factor-related apoptosis-inducing ligand in human colon carcinoma COLO205 tumor-bearing nude mice", Drug Metab Dispo., 32(11):1230-8 (2004).
Yao, et al., "Intra-articular adenoviral-mediated gene transfer of trail induces apoptosis of arthritic rabbit synovium", Gene therapy, 10(12):1055-60 (2003).
Yoshioka, et al., "Optimal site-specific PEGylation of mutant TNF-alpha improves its antitumor potency", Biochem Biophys Res Comm., 315:808-14 (2004).
Youn, et al., "Biological and physicochemical evaluation of the conformational stability of tumor necrosis factor-related apoptosis-inducing ligand (TRAIL)", Biotechnol. Lttrs., 29:713-21 (2007).
Youn, et al., "PEGylated apoptotic protein-loaded PLGA microspheres for cancer therapy", International Journal of Nanomedicine, 2015:739 (2015).
Zemel, "Dietary Calcium and Dairy Products Modulate Oxidative and Inflammatory Stress in Mice and Humans", Journal of Nutrition, 138:1047-1052 (2008).
Zhu, et al., "A Novel Therapeutic Approach Targeting TRAIL signaling reveals a role for activated pancreatic stellate cells in the pathogenesis of pain in chronic pancreatitis", Gastroenterology, 150(4):S916-S917 (2016).
Zhu, et al., "Transforming growth factor beta induces sensory neuronal hyperexcitability, and contributes to pancreatic pain and hyperalgesia in rats with chronic pancreatitis", Mol Pain, 8:65 (2012).

Azab, et al., "Elevated serum TRAIL levels in scloderma patients and its possible association with pulmonary involvement", Clinical Rheumatology; Journal of the International League of Associations for Rheumatology, 31(9):1359-1364 (2012).
Castellino, et al., "The tumor necrosis factor-related apoptosis-inducing ligand-osteoprotegerin system in limited systemic sclerosis: a new disease marker", Rheumatology, 49(6):1173-1176 (2010).
Gilbane, et al., "Scleroderma pathogenesis: a pivotal role for fibroblasts as effector cells", https://www/ncbi.nlm.nih.gov/pmc/articles/PMC4060542/pdf/ar4230.pdf retreived on Jul. 3, 2019, Arth. Res 15:215 (2013).
Jiang, et al., "PEGylated TNF-related apoptosis-inducing lgands (TRAIL) for effective tumor combination therapy", Biomaterials, 32:8529-8537 (2011).
Park, et al., "Targeting of dermal myofibroblasts through death receptor 5 arrests fibrosis in mouse models of scleroderma", Nature Communications, 10(1) (2019).
Klonowski-Stumpe, et al., "Apoptosis in activated rat panreatic stellate cells", Am. J. Physiol. Gastrointest. Liver Physiol., 283:819-826 (2002).
Pan, et al., "site-specific PEGylation of a mutated-cysteine residue and its effect on tumor necrosis factor (TNF)-related apoptosis0inducing ligand (TRAIL)", Biomaterials, 34(36): 9115-9123 (2013).
Ichikawa, et al., "TRAIL-R2(DR5) mediates apoptosis if synovial fibroblasts in rheumatoid arthritis", J. Immunol., 171:1061-69 (2003).
Tisato, et al., "Clinical perspectives of trail: insights into central nervous disorders", Cell. Mol. Life Sci., 73(24):2017-2027 (2016).
Tisato, et al., "Intranasal administration of recombinant TRAIL down-regulates CXCL-1/KC in an ovalbumin-induced airway inflammation murine model", PLoS One, 9(12):e115387 (2014).
Bachem, et al. "Chapter 38: Fibrogenesis of the pancreas: the role of stellate cells", The Pancreas: An Integrated Textbook of Basic Science, Medicine, and Surgery, Second Edition Edited by Beger et al., Blackwell Publishing Limited, 383-392, (2008).
Bhanot, et al., "Dichotomy of fates of pancreatic epithelia in chronic pancreatitis: apoptosis versus survival", Trends in Molecular Medicine, 12(8):351-357 (2006).
Dumnicka, et al., "Osteoprotegerin, trail and osteoprotegerin/ trail ratio in patients at early phase of acute pancreatitis.", Folia Medica Cracoviensia, 54(2):17-26 (2014).
Hironobu, "Updated Diagnosis/severity criteria of intractable systemic autoimmune disease, Systemic scleroderma", Inflammation & Immunity, 23(6):517-521 (Oct. 2015) with English Summary.
Johns Hopkins Medicine, FAQs about Chronic Pancreatitis, [Retrieved online Sep. 18, 2020] <URL:]https://www.hopkinsmedicine.org/gastroenterology_hepatology/diseases_conditions/faqs/chronic_pancreatitis.html>(2020).
Li, et al., "The role of TRAIL signal pathway in acute pancreatitis", Hepato-Gastroenterology, 60(124):912-915 (2013).
Mews, et al., "Pancreatic stellate cells respond to inflammatory cytokines: otential role in chronic pancreatitis", Gut, 50:535-541 (2002).
Zheng, et al., "Role of immune cells and immune-based therapies in pancreatitis and pancreatic ductal adenocarinoma", Gastroenterol. 144: 1230-1240, (2013).

\* cited by examiner

AMELIORATING SYSTEMIC SCLEROSIS WITH DEATH RECEPTOR AGONISTS

CROSS REFERENCE TO RELATED APPLICATIONS

This application is a National Phase application under 35 U.S.C. 371 of PCT/US2016/067145, filed Dec. 16, 2016, entitled "AMELIORATING SYSTEMIC SCLEROSIS WITH DEATH RECEPTOR AGONISTS", which claims the benefit of priority under 35 U.S.C. § 119(e) to U.S. Provisional Application No. 62/268,637, filed Dec. 17, 2015, which are hereby incorporated herein by reference in its their entirety.

STATEMENT REGARDING FEDERALLY SPONSORED RESEARCH

This invention was made with government support under W81XWH-14-1-0239 awarded by the Army Medical Research and Material Command. The government has certain rights in the invention.

REFERENCE TO SEQUENCE LISTING

The Sequence Listing submitted as a text file named "JHU_C_13722_ST25.txt," created on Dec. 14, 2016, and having a size of 2,872 bytes is hereby incorporated by reference pursuant to 37 C.F.R. § 1.52(eX5).

FIELD OF THE INVENTION

The invention is generally directed to compositions and methods for treating autoimmune fibrotic disease with death receptor agonists.

BACKGROUND OF THE INVENTION

Fibrosis refers to a condition caused by loss of normal function due to tissue sclerosis, in which a mass of a connective tissue, including tissue components such as collagen, is increased and a normal tissue is replaced by the connective tissue. Fibrosis can occur in the liver, lung, kidney, heart, skin, and in other tissues.

Systemic sclerosis (SSc), also known as scleroderma, is a rare autoimmune and rheumatic disorder (McMahan Z H et al., *Nat Rev Rhuematol;* 9(2):90-100 (20130 and Varga J et al., *J. Clin Invest;* 117(3):557-567 (2007)). SSc induces hardening of connective tissues by fibrosis (Ho Y Y et al., *Nat Rev Rheumatol;* 10(7):390-402 (20140 and Bhattacharyya S et al., *Nat Rev Rheumatol;* 8(1):42-54 (2012)), an accumulation of extracellular matrix (ECM) proteins, which affects the skin of the most visible body parts such as face and hands, and in the diffuse form, can lead to severe dysfunction and failure of almost any internal organ including the lungs, heart, kidneys and stomach. Accordingly, symptoms of this immune disease include fibrosis of the skin and internal organs, including, liver, lung, kidney, gastrointestinal tract, and heart. These symptoms can often be debilitating for the patient. The SSc prevalence varies widely across the world with an estimated 2.5 million patients. It has the highest death rate of any rheumatic condition with no standard of care (Nikpour M et al., *Curr Opin Rheumatol:*26(2):131-137 (2014)). Prior to the disclosure herein, there were no therapies that ameliorate and/or prevent skin fibrosis and fibrosis of internal organs affected by SSc. As such, there is a significant unmet need for SSc therapy since no drugs have emerged.

SUMMARY OF THE INVENTION

The present disclosure is based, at least in part, upon the identification of compositions and methods for treating or preventing fibrotic autoimmune disease or disorders, such as systemic sclerosis (SSc). Without wishing to be bound by theory, the methods and compositions of the disclosure are believed to act by selectively targeting myofibroblasts (e.g., activated fibroblasts), which are key cells involved in the establishment and/or progression of fibrotic diseases, such as SSc and/or fibrotic conditions of the liver, lung, kidney, heart, gastrointestinal tract, skin, with such fibrotic conditions optionally associated with conditions such as SSc. The therapeutic strategy set forth herein is based upon the identification and use of agents that are death receptor (DR) agonists, variants and/or derivatives thereof, as well as synthetic compounds, and optionally other mimics of naturally-occurring DR agonists.

In one aspect, the disclosure provides a method for treating or preventing a fibrotic autoimmune disease or disorder in a mammalian subject, by administering to the subject a death receptor agonist in an amount effective to reduce or prevent fibrosis in the subject, thereby treating the fibrotic autoimmune disease or disorder in the subject.

In one embodiment, the disclosure provides a method of treating or preventing a fibrotic autoimmune diseases or disorder in a mammalian subject. The method includes administering a death receptor agonist to the subject to inhibit and block fibroblast activation (transition into myofibroblasts), or to deplete activated myofibroblasts through targeting upregulated death receptors on activated fibroblasts and/or profibrogenic cells. Examples of death receptor agonists include TRAIL and agonistic death receptor antibodies, as well as their analogues, variants, fragments, and derivatives. Examples of activated fibroblasts and/or profibrogenic cells include pericytes and fibrocytes during disease progression.

In one embodiment, the fibrotic autoimmune disease is systemic sclerosis (SSc). In a further embodiment the SSc is limited scleroderma or diffuse scleroderma.

In certain embodiments, the DR agonist is or includes a tumor necrosis factor (TNF)-related apoptosis-inducing ligand (TRAIL), a TRAIL analogue, DR agonistic antibodies, or a derivative thereof. In further embodiments, the DR agonist is or includes a human recombinant TRAIL, a human TRAIL analogue, or a derivative thereof, or the DR agonist is or includes native TRAIL, a native TRAIL analogue, or a derivative thereof. In another embodiment, the DR agonist includes one or more of DR4 or DR5 agonists selected from the group consisting of an antibody, a chimeric antibody, an antibody fragment, a fusion protein, and a multivalent agent.

Another embodiment of the disclosure provides for the DR agonist attached to a polymer. In related embodiments, the polymer is polyethylene glycol (PEG), or derivative thereof. The PEG or its derivative may be methoxypolyethylene glcycol succinimidyl propionate, methoxypolyethylene glycol succinate N-hydroxysuccinimide, methoxypolyethylene glycol propionaldehyde, and methoxypolyethylene glycol maleimide. The PEG and its derivative may be of linear and/or multiple-branched type. Branched polymers include di-branched, tri-branched, multi-arm, dimeric, and trimeric structures.

The PEG or derivative thereof has a molecular weight of between about 1,000 Da and 100,000 Da. In a further embodiment, the PEG or derivative thereof has a molecular weight of between about 5,000 and 50,000. The molecular weight of the PEG or its derivative may be between about 5,000 and 70,000 Da, or between about 20,000 and 50,000 Da, or any molecular weight falling within the range of between 1,000 Da and 100,000 Da.

The DR agonist may be administered systemically, enterally, parenterally, locally, or via buccal delivery. The DR agonist may be administered locally, such as topically or subcutaneously.

In one embodiment, dermal thickness, the levels of skin collagen, TGF-β, PDGFs, PDGF receptors, CTGF, and/or α-SMA$^+$ fibroblastic cells are reduced, maintained at, or restored to, normal levels in the subject, as compared to an appropriate control.

In another embodiment, fibrosis is treated or prevented in the subject, as compared to an appropriate control.

In an additional embodiment, the death receptor agonist is administered by injection at a dosage of between 0.01 mg/kg and 50 mg/kg to the subject, e.g., 0.1 to 50 mg/kg. e.g., 1 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, or 50 mg/kg. In certain embodiments, the death receptor agonist is administered in one or more dosages. Optionally, the death receptor agonist is administered to the subject over a period of one or more days, e.g., 1 day, 2 days, 3 days, 4 days, 5 days, 6 days, 7 days, 8 days, 9 days 10 days, 15 days, 20 days, 25 days, 1 month, 2 months, 3 months 6 months, 1 year, or more. In some cases, the death receptor agonist is administered daily. In other cases, the death receptor agonist is administered every other day.

In another embodiment, the subject is human. In some cases, the subject is identified as having or at risk of developing a fibrotic autoimmune disease or disorder.

The disclosure also provides for an injectable pharmaceutical composition for treatment or prevention of a systemic fibrotic disease or disorder in a mammalian subject that includes a death receptor agonist at a concentration of 0.1 to 50 mg/kg or between 0.001% and 50% and a pharmaceutically acceptable carrier.

DETAILED DESCRIPTION OF THE INVENTION

I. Definitions

Figure 1:
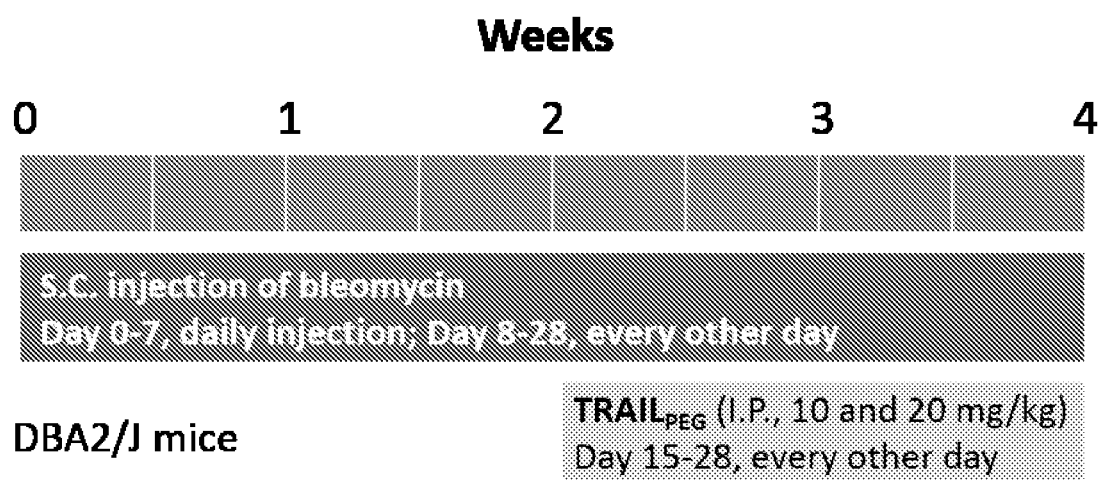
FIG. 1 depicts a schematic of the study design for the in vivo mouse model studies of bleomycin-induced systemic sclerosis.

As used herein, a "fibrotic autoimmune disease or disorder" refers to any autoimmune disease or disorder that is characterized by fibrosis. Systemic sclerosis (SSc; scleroderma) is an exemplary form of fibrotic autoimmune disease or disorder, as is any autoimmune-mediated fibrosis of the liver, lung, kidney, heart, gastrointestinal tract, skin, etc.

The term "antibody" may refer to a polyclonal antisera or monoclonal antibody. Antibodies described herein encompass not only an intact monoclonal antibody, but also an immunologically-active antibody fragment, e. g., a Fab or (Fab)2 fragment; an engineered single chain FV molecule; or a chimeric molecule, e.g., an antibody which contains the binding specificity of one antibody, e.g., of murine origin, and the remaining portions of another antibody, e.g., of human origin. Antibodies described herein also include a humanized antibody, wherein the antibody is from a non-human species, whose protein sequence has been modified to increase their similarity to antibody variants produced naturally in humans. Generally, a humanized antibody has one or more amino acid residues introduced into it from a source which is non-human. These non-human amino acid residues are referred to herein as "import" residues, which are typically taken from an "import" antibody domain, particularly a variable domain.

An "agonist" as used herein is a molecule which enhances the biological function of a protein. The agonist may thereby bind to the target protein to elicit its functions. However, agonists which do not bind the protein are also envisioned. The agonist may enhance or activate the biological function of the protein directly or indirectly. Agonists which increase expression of certain genes are envisioned within the scope of particular embodiments of the disclosure. Suitable agonists will be evident to those of skill in the art. For the present disclosure it is not necessary that the agonist enhances the function of the target protein directly. Rather, agonists are also envisioned which stabilize or enhance the function of one or more proteins upstream in a pathway that eventually leads to activation of targeted protein. Alternatively, the agonist may inhibit the function of a negative transcriptional regulator of the target protein, wherein the transcriptional regulator acts upstream in a pathway that eventually represses transcription of the target protein.

"Death receptors" form a subclass of the Tumor Necrosis Factor Receptor (TNFR) superfamily which encompasses eight members: Fas, TNFR1, neurotrophin receptor (p75NTR), ectodysplasin-A receptor (EDAR), death receptor (DR) 3, DR4, DR5, and DR6. Most of the death receptors have their corresponding natural ligands identified: TNFR1 can be activated by TNF, Fas is activated by Fas ligand (FasL), p75NTR is activated by nerve growth factor (NGF, gene ID: 4803). One ligand for EDAR is ectodysplasin-A (EDA, gene ID: 1896). DR3 can be activated by Apo3L (TWEAK/TNFSF12, gene ID: 8742), TL1A/VEG1 (vascular endothelial growth inhibitor/TNFSF15, gene ID: 9966), while DR4 and DR5 share the same ligand, TNF-related apoptosis-inducing ligand (TRAIL). The ligand for DR6 has not been identified. These ligands, their variants or any molecule that mimic the effect of the natural ligand is considered as a death receptor agonist. Each of these natural ligands and agonists thereof is considered a death receptor agonist.

A "death receptor agonist" is defined herein as any molecule which is capable of inducing pro-apoptotic signaling through one or more of the death receptors. The death receptor agonist may be selected from the group consisting of antibodies, death ligands, cytokines, death receptor agonist expressing vectors, peptides, small molecule agonists, cells (for example stem cells) expressing the death receptor agonist, and drugs inducing the expression of death ligands.

Exemplary death receptor agonists are capable of binding to a death receptor and inducing apoptosis or programmed cell death through one or more intracellular pathways. Exemplary well studied death receptor agonists include members of the TNF ligand family, which can play key roles in regulatory and deleterious effects on immune tolerance, in addition to both protective and pathogenic effects on tissues (Rieux-Laucat et al., 2003, *Current Opinion in Immunology* 15:325; Mackay and Ambrose, 2003, *Cytokine and growth factor reviews,* 14: 311; Mackay and Railed, 2002, *Current Opinion in Immunology.* 14: 783-790). Examples of such proteins include Tumor necrosis factor-related apoptosis inducing ligand (TRAIL), Fas ligand (FasL) and Tumor Necrosis Factor (TNF). Exemplary death receptor agonists induce apoptosis upon binding to transmembrane, death domain containing receptors. For example, TRAIL binds to death receptor 4 (DR4; TRAIL receptor 1) and 5 (DR5; TRAIL receptor 2). Three other TRAIL-binding receptors exist, but are considered to be "decoy receptors" as they appear to be unable to transmit an apoptotic signal. Decoy receptor 1 (DcR1) appears to lack the transmembrane and intracellular domains and is anchored to the plasma membrane via a glycosylphosphatidylinositol-tail. Decoy receptor 2 (DcR2) possesses a truncated and apparently non-functional death domain, while the third decoy receptor, osteoprotegerin is a secreted, soluble receptor. Fas ligand induces apoptosis by binding to Fas (also known as CD95 or Apo-1), while DcR3 sequesters FasL from Fas. Another death receptor agonist, TNF can induce apoptosis by binding to TNF-receptor I (also known as TNFRI or TNFR55).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

A "Tumor Necrosis Factor family member" or a "Tumor Necrosis Factor ligand family member" is any cytokine which is capable of activating a Tumor Necrosis Factor receptor. "TRAIL protein", as used herein, encompasses both the wild-type TRAIL protein and TRAIL variants.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

For example, by "variant" death receptor agonist it is meant that the death receptor agonist differs in at least one amino acid position from the wild type sequence of the death receptor agonist. By "variant" TRAIL protein it is meant that the TRAIL protein differs in at least one amino acid position from the wild type TRAIL protein (also known as TNFSFIO, TL2; APO2L; CD253; Apo-2L), Entrez GeneID: 8743; accession number NM_003810.2; UniProtKB/Swiss-Prot: P50591; UniProtKB/TrEMBL: Q6IBA9.

By "agent" is meant any small compound, antibody, nucleic acid molecule, or polypeptide, or fragments thereof.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease or disorder, and the treatment being administered. The effect of the effective amount can be relative to a control. Such controls are known in the art and discussed herein, and can be, for example, the condition of the subject prior to or in the absence of administration of the drug, or drug combination, or in the case of drug combinations, the effect of the combination can be compared to the effect of administration of only one of the drugs. The control can also be a subject in need of the drug/treatment but who did not receive the drug/treatment.

By "ameliorate" is meant decrease, suppress, attenuate, diminish, arrest, or stabilize the development or progression of a disease.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "marker" is meant any protein or polynucleotide having an alteration in expression level or activity that is associated with a disease or disorder.

The term "reduce", "inhibit". "alleviate" or "decrease" are used relative to a control. One of skill in the art would readily identify the appropriate control to use for each experiment. For example a decreased response in a subject or cell treated with a compound is compared to a response in subject or cell that is not treated with the compound.

By "modulate" is meant alter (increase or decrease). Such alterations are detected by standard art known methods such as those described herein.

Ranges provided herein are understood to be shorthand for all of the values within the range. For example, a range of between 1 and 50 is understood to include any number, combination of numbers, or sub-range including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "recombinant host cell" or "host cell" refers to a cell that includes an exogenous polynucleotide, regardless of the method used for insertion, for example, direct uptake, transduction, or other methods known in the art to create recombinant host cells. The exogenous polynucleotide may be maintained as a nonintegrated vector, for example, a plasmid, or alternatively, may be integrated into the host genome. As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which TRAIL has been secreted, including medium either before or after a proliferation step. The term also may encompass buffers or reagents that contain host cell lysates, such as in the case where TRAIL is produced intracellularly and the host cells are lysed or disrupted to release TRAIL.

By "reduces" is meant a negative alteration of at least 10%, 25%, 50%, 75%, or 100%.

As used herein, "obtaining" as in "obtaining an agent" includes synthesizing, purchasing, or otherwise acquiring the agent.

By "subject" is meant a mammal, including, but not limited to, a human or non-human mammal, such as a bovine, equine, canine, ovine, or feline.

The term "TRAIL" also includes TRAIL heterodimers, homodimers, heteromultimers, or homomultimers of any one or more TRAIL or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

As used herein, the terms "treat." treating," "treatment," and the like refer to reducing or ameliorating a disorder and/or symptoms (e.g., fibrosis) associated therewith. It will be appreciated that, although not precluded, treating a disorder or condition does not require that the disorder, condition or symptoms associated therewith be completely eliminated.

As used herein, the terms "prevent," "preventing," "prevention." "prophylactic treatment" and the like refer to reducing the probability of developing a disorder or condition in a subject, who does not have, but is at risk of or susceptible to developing a disorder or condition.

By "reference" is meant a standard or control condition.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%., or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent to those skilled in the art from the following detailed description and claims.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

II. Compositions

TRAIL (tumor necrosis factor-related apoptosis-inducing ligand, gene name TNFSF10) is a death ligand that can induce apoptosis in cells expressing its cognate death receptors (DRs), DR4 (gene name TNFRSF10A) and DR5 (gene name TNFRSF10B) (Johnstone R W et al., *Nat Rev Cancer;* 8(10):782-798 (2008)). Due to its unique ability to selectively induce DR-mediated apoptosis in DR+ cancer cells while showing no apparent toxicity to normal cells, the recombinant TRAIL and DR agonistic antibodies have been actively studied for cancer therapy. Clinical studies of TRAIL revealed a broad tolerability in humans but failed to demonstrate a robust therapeutic benefit in oncology (Lemke J et al., *Cell Death Differ;* 21(9):1350-1364 (2014)). The main factors responsible for the disappointing results of TRAIL used in cancer patients are 1) its short half-life (less than 30 min in humans) and 2) heterogeneous primary cancers are generally TRAIL-resistant. Activated primary human hepatic and pancreatic stellate cells, but not quiescent stellate cells, become highly sensitive to TRAIL-induced apoptosis due to upregulated DR4 and DR5 (US patent application publication No. US 2016/0022776). Activated HSCs and PSCs are considered the progenitors of liver and pancreatic fibrosis.

The pathogenic mechanisms underlying fibrosis in SSc are complex and largely unknown. However, myofibroblasts (MFBs) are clearly one of the significant originators of this disorder (Ho Y Y et al., *Nat Rev Rheumatol;* 10(7):390-402 (2014) and Bhattacharyya S et al., *Nat Rev Rheumatol;* 8(1):42-54 (2012)). During chronic skin damage or disease, resident fibroblasts undergo activation and convert to proliferative, fibrogenic and contractile α-SMA+MFBs, which accumulate at the leading edge of active fibrosis. MFBs have increased capacity to synthesize collagen and other ECM components as well as multiple fibrogenic components to orchestrate and perpetuate skin fibrogenesis. By nature. MFBs are a major upstream target for skin fibrosis/SSc therapy. Therefore, designing a highly selective agent that can eliminate the progenitors of SSc, MFBs, while sparing normal cells, could produce marked antifibrotic effects. However, the lack of robust ways to selectively target MFBs in the body hampers this strategy. A new strategy to deplete α-SMA+MFBs during SSc progression while leaving normal cells unharmed is needed.

There is a need for therapies that ameliorate and/or prevent skin fibrosis and fibrosis of internal organs affected by systemic sclerosis.

Therefore, it is an object of the invention to provide compositions and methods for treating or preventing systemic sclerosis without off-target toxicity.

It is another object of the invention to provide compositions and methods for reducing or blocking fibroblast or profibrogenic cell activation in systemic sclerosis while leaving normal cells unharmed.

It is another object of the invention to provide compositions and methods for reducing or depleting myofibroblasts in systemic sclerosis while leaving normal cells unharmed.

The disclosure is based, at least in part, upon the discovery of death receptor (DR) agonists (e.g., TRAIL and DR agonistic antibodies), as a therapeutic and/or preventive modality, either as native agonist agents or a variant or derivative thereof, for treatment and/or prevention of a fibrotic autoimmune disease or disorder (e.g., SSc) in a mammalian subject. A primary goal of the studies set forth herein involved identification of TNF-related apoptosis-inducing ligand (TRAIL) receptor agonists (TRA) (e.g., recombinant TRAIL variants and antibodies) as anti-fibrotic and/or anti-inflammatory agents for targeting local and diffuse SSc. In certain embodiments, the disclosure therefore describes a unique mechanism of action that targets and blocks key fibrogenic cell activation into myofibroblasts (MFBs), or eradicates key fibrogenic cells to reverse fibrosis and resolve inflammation in SSc.

The studies disclosed herein show that death receptor agonists can induce TRAIL-mediated apoptosis of activated fibroblasts and myofibroblasts, in SSc. Importantly, DR agonists including TRAIL analog and DR antibody strongly ameliorate fibrosis and inflammation in complementary SSc models by selectively blocking fibroblast activation and depleting α-SMA+MFBs, and simultaneously down-regulating multiple fibrogenic components without notable toxicity.

This disclosure proves that blocking MFB activation and depleting MFBs, the predominant profibrogenic cell population, through upregulated DRs either induces resolution or prevents progression of advanced fibrosis in SSc. TGF-activated, α-SMA+ primary human fibroblasts spontaneously become susceptible to TRAIL and DR agonistic antibody through DR-mediated apoptosis. Unlike certain types of primary cancer cells, activated MFBs were not resistant to TRAIL. In complementary two SSc mouse models, studies validated that DR4 and DR5 are highly upregulated on α-SMA+MFBs in fibrotic skin tissues compared to that of normal skin tissues. When SSc animal models were treated with both TRAIL analog and DR antibody, it was found that DR agonists target MFBs in vivo and clearly ameliorate advanced fibrosis without off-target toxicity. Moreover, tissue fibrosis in skin biopsies from healthy subjects and patients with SSc was analyzed. In normal skin tissues, no strong α-SMA and DRs expression was observed. In contrast, higher levels of DR4 and DR5 as well as α-SMA in fibrotic skin tissues from SSc patients was detected. This disclosure provides new insight and clinical rationale for a novel treatment of SSc.

Using primary human tissues from SSc patients and animal models of SSc, TRAIL receptor analogs (TRAs) reversed fibrosis and the extensive inflammatory response associated with SSc. Based on preclinical data, systemically administered $TRAIL_{PEG}$, a PEGylated recombinant human homotrimeric TRAIL, and anti-DR antibody targeted alpha smooth muscle actin-positive (α-SMA$^+$) myofibroblasts in vivo to simultaneously inhibit multiple fibrogenic molecules in SSc. In rodent SSc models, $TRAIL_{PEG}$ and anti-DR antibody reduced skin hardening and excess collagen production back to healthy levels. Similarly, $TRAIL_{PEG}$; and anti-DR antibody reduced extensive fibrosis in idiopathic pulmonary fibrosis, a possible symptom of SSc.

During tissue damage, inflammation and auto-antibodies activate fibroblasts into myofibroblasts, which induce fibrosis. Recruited cells, such as fibrocytes, bone marrow mesenchymal stem cells and pericytes also transdifferentiate into myofibroblasts during fibrosis progression. $TRAIL_{PEG}$ and anti-DR antibody appeared to have targeted and blocked such activation and induced TRAIL-mediated cell death only in myofibroblasts, but not normal cells, as well as ameliorated the inflammatory response that activates myofibroblasts. As a result, the fibrogenic pathway was halted and healthy fibroblasts repopulated the organ. Without wishing to be bound by theory, DR agonists including $TRAIL_{PEG}$ and anti-DR antibodies was therefore believed to have targeted the myofibroblast cell population and demonstrated its ability to reverse SSc by addressing all fibroblast activation mechanisms, including autoimmune, inflammation and transdifferentiation mechanisms.

Additional features of the disclosed method are set forth below and elsewhere herein.

A. Death Receptor Agonists

Death receptor agonists described herein include TRAIL and agonistic death receptor antibodies, as well as their analogues, variants, fragments, and derivatives.

1. TRAIL

Tumor necrosis factor (TNF)-related apoptosis-inducing ligand (TRAIL) is a member of the TNF family, and is a transmembrane protein that participates in apoptosis. TRAIL is a protein consisting of 281 amino acids in which an extracellular domain includes amino acids from arginine at position 115 to glycine at position 281 or threonine at position 95 to glycine at position 281 affects apoptosis.

The human TRAIL protein sequence is available as REFSEQ accession NP_003801 and is provided below (SEQ ID NO: 1):

```
MAMMEVQGGPSLGQTCVLIVIFTVLLQSLCVAVTYVYFTNELKQMQDKYS

KSGIACFLKEDDSYWDPNDEESMNSPCWQVKWQLRQLVRKMILRTSEETI

STVQEKQQNISPLVRERGPQRVAAHITGTRGRSNTLSSPNSKNEKALGRK

INSWESSRSGHSFLSNLHLRNGELVIHEKGFYYIYSQTYFRFQEEIKENT

KNDKQMVQYIYKYTSYPDPILLMKSARNSCWSKDAEYGLYSIYQGGIFEL

KENDRIFVSVTNEHLIDMDHEASFFGAFLVG
```

Three molecules of TRAIL monomer form a structurally modified trimer. The TRAIL trimer assembles with receptors participating in cell death to induce apoptosis. A major difference between TRAIL and other members of the TNF superfamily is its ability not to induce cell death at normal tissues. Since TNF affects normal cells and also induces the death of cancer cells and over-activated immune cells, it has limited applicability. In contrast, TRAIL induces apoptosis in a wide range of cancer cells and over-activated immune cells with little effect on normal cells. This is due to the differential expression of TRAIL receptors between cell types.

TRAIL induces apoptosis through interacting with its receptors. Currently, 4 human receptors for TRAIL have been identified, including death receptor 4 (DR4), death receptor 5 (DR5), decoy receptor 1 (DcR1), decoy receptor 2 (DcR2), and osteoprotegrin (OPG). TRAIL induces death via caspase-dependent apoptosis upon binding to DR4 and DR5, which both contain a conserved death domain (DD) motif. DcR1 and DcR2 act as decoys for their ability to inhibit TRAIL-induced apoptosis when overexpressed. DcR1 and DcR2 have close homology to the extracellular domains of DR4 and DR5. DcR2 has a truncated, nonfunctional cytoplasmic DD, while DcR1 lacks a cytosolic region and is anchored to the plasma membrane through a glycophospholipid moiety. The cytoplasmic domain of DcR2 is functional and activates NF-κB which leadings to transcription of genes known to antagonize the death signaling pathway and/or to promote inflammation. Ligand binding to DR4 triggers receptor trimerization and clustering of its intracellular death domains, resulting in the formation of a death inducing complex (DISC). The DISC recruits adaptor molecules and initiates the binding and activation of caspases to induce apoptosis. Inducing or restoring signaling through TRAIL receptors is an anticancer strategy; TRAIL has also been shown to inhibit auto antigen-specific T cells indicating that it may suppress autoimmune responses. In addition to toxicity toward some normal cells. TRAIL has a short half-life in vivo, and has different half-lives according to the species of animals used in tests. For example, TRAIL has been reported to have a half-life of several minutes in rodents and about 30 minutes in apes (H. Xiang, et al. Drug Metabolism and Disposition 2004, 32, 1230-1238). In particular, most of TRAIL is rapidly excreted via the kidneys.

a. TRAIL Analogues

TRAIL can interact with its receptors as a trimer. Therefore, in some embodiments, the ligand or agonist used in the methods disclosed herein is, or can form, a multimer, preferably a trimer. The trimer can be a homotrimer, or a heterotrimer.

All of the TRAIL proteins described herein can be made using standard techniques for isolation of natural or recombinant proteins, and chemically modified as described herein.

The TRAIL conjugate can include a TRAIL analogue, or an agonistic TRAIL receptor binding fragment or variant thereof. TRAIL analogues are known in the art. In preferred embodiments, the analogues have increased affinity or specificity for one or more agonistic TRAIL receptors (e.g., TRAILR1 (DR4) and/or TRAIL-R2 (DR5)), reduced affinity or specificity for one or more antagonistic or decoy TRAIL receptors (e.g., receptors DcR1 and DcR2) or a combination thereof compared to wild-type or endogenous TRAIL.

In some embodiments, the analogue is a DR4-selective mutant of wild-type TRAIL. DR-4 selective mutants are known in the art and disclosed in, for example, Tur, *J. Biological Chemistry*, 283(29):20560-8 (2008). In a particular embodiment, the analogue is a variant of SEQ ID NO: 1 having a D218H or a D218Y substitution, or a functional fragment thereof (e.g., the extracellular domain).

In some embodiments, the analogue is a DR5-selective mutant of wild type TRAIL. Particular DR-S-selective mutants include variants of SEQ ID NO:1 having D269H, D269H/E 95R, or D269H/T214R, and functional fragments thereof (e.g., the extracellular domain). Such variants are described in van der Sloot, *Proc. Nat. Acad Sci. USA* 103(23):8634-9 (2006).

b. TRAIL Fusion Proteins

The TRAIL conjugate can be a TRAIL fusion protein. TRAIL fusion polypeptides have a first fusion partner including all or a part of a TRAIL protein extracellular domain fused (i) directly to a second polypeptide or, (ii) optionally, fused to a linker peptide sequence that is fused to the second polypeptide. The fusion proteins optionally contain a domain that functions to dimerize or multimerize two or more fusion proteins. The peptide/polypeptide linker domain can either be a separate domain, or alternatively can be contained within one of the other domains (TRAIL polypeptide or second polypeptide) of the fusion protein. Similarly, the domain that functions to dimerize or multimerize the fusion proteins can either be a separate domain, or alternatively can be contained within one of the other domains (TRAIL polypeptide, second polypeptide or peptide/polypeptide linker domain) of the fusion protein. In one embodiment, the dimerization/multimerization domain and the peptide/polypeptide linker domain are the same.

Fusion proteins disclosed herein can be of formula I:

N—R1-R2-R3-C wherein "N" represents the N-terminus of the fusion protein, "C" represents the C-terminus of the fusion protein, "R1" is a TRAIL polypeptide, "R2" is an optional peptide/polypeptide linker domain, and "R3" is a second polypeptide. Alternatively, R3 may be the TRAIL polypeptide and R1 may be the second polypeptide.

The fusion proteins can be dimerized or multimerized. Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

The presence of the second polypeptide can alter the solubility, stability, affinity and/or valency of the TRAIL fusion polypeptide. As used herein. "valency" refers to the number of binding sites available per molecule. In some embodiments, the second polypeptide contains one or more domains of an immunoglobulin heavy chain constant region, preferably having an amino acid sequence corresponding to the hinge, CH2 and CH3 regions of a human immunoglobulin Cγ1 chain or to the hinge, CH2 and CH3 regions of a murine immunoglobulin Cγ2a chain. In a particular dimeric fusion protein, the dimer results from the covalent bonding of Cys residue in the hinge region of two of the Ig heavy chains that are the same Cys residues that are disulfide linked in dimerized normal Ig heavy chains.

In a particular embodiment, the TRAIL fusion protein is a TRAIL-mimic including three TRAIL-protomer subsequences combined in one polypeptide chain, termed the single-chain TRAIL-receptor-binding domain (scTRAIL-RBD), as described in Gieffers, *Molecular Cancer Therapeutics*, 12(12):273547 (2013). Two of the so-called scTRAIL-RBDs, with three receptor binding sites each, can be brought in close proximity resulting in a multimeric fusion protein with a hexavalent binding mode. In some embodiments, multimerization is achieved by fusing the Fc-part of a human immunoglobulin G1 (IgG1)-mutein C-terminally to the scTRAIL-RBD polypeptide, thereby creating six receptor binding sites per drug molecule.

Forcing dimerization of scFv-scTRAIL based on scFv linker modification for a targeted scTRAIL composed predominantly of dimers (DbscTRAIL) exceed the activity of nontargeted scTRAIL approximately 100-fold for some target cell types. Increased activity of DbscTRAIL was also demonstrated on target-negative cells, indicating that, in addition to targeting, oligomerization equivalent to an at least dimeric assembly of standard TRAIL per se enhances apoptosis signaling. Therefore, in preferred embodiments, the TRAIL fusion proteins have a multimerization domain, such as a dimerization or trimerization domain, or a combination thereof that can lead to, for example, dimeric, trimeric, or hexameric molecule.

Another fusion protein that facilitates trimer formation includes a receptor binding fragment of TRAIL aminoterminally fused to a trimerizing leucine or isoleucine zipper domain.

TRAIL fusion proteins and results of using the fusion proteins in functional assays are also described in, Wahl, *Hepatology*, 57(2):625-36 (2013).

2. $TRAIL_{PEG}$: PEGylated TRAIL
a. Polyethylene Glycol

Polyethylene glycol (PEG) is a polymer having a structure of HO—(—$CH_2CH_2O$-)n-H when in linear form. Due to its high hydrophilicity, PEG enables an increase in the solubility of drug proteins when linked thereto. In addition, when suitably linked to a protein, PEG increases the molecular weight of the modified protein while maintaining major biological functions, such as enzyme activity and receptor binding; thereby reducing urinary excretion, protecting the protein from cells and antibodies recognizing exogenous antigens, and decreasing protein degradation by proteases. The molecular weight of PEG, capable of being linked to proteins, ranges from between about 1,000 and 100,000. PEG having a molecular weight higher than 1,000 is known to have very low toxicity. PEG having a molecular weight between 1,000 and 6.000 is distributed widely throughout the entire body and is metabolized via the kidney. In particular, PEG having a molecular weight of 40,000 is distributed in the blood and organs, including the liver, and is metabolized in the liver. Exemplary PEG or PEG derivatives include but are not limited to: methoxypolyethylene glcycol succinimidyl propionate, methoxypolyethylene glycol succinate N-hydroxysuccinimide, methoxypolyethylene glycol propionaldehyde, methoxypolyethylene glycol maleimide, and multiple-branched polyethylene glycol.

In this regard, PEG was selectively attached at the N-terminus of TRAIL as described in international publication number WO 2007/145457, incorporated herein by reference. Additionally, PEGylation remarkably increased the solubility and stability of TRAIL (e.g., the stability, half-life and in vivo activity of PEGylated TRAIL was significantly greater than native-type TRAIL). Also, PEGylation was found to improve pharmacokinetic profiles of a linked drug with long-term storage in various formulations, thereby reducing drug administration frequencies and allowing sustained duration of effects of the drug.

Non-linear forms of PEG or its derivative may also be used. Examples include branched polymers, such as di-branched, tri-branched, multi-arm, dimeric, and trimeric structures.

I. Polyalkylene Oxides and TRAIL

The use of hydrophilic polymers such as polyalkylene oxides, or copolymers thereof such as the PLURONIC®s sold by BASF can be covalently bound to the molecules to improve the pharmacokinetic and pharmacodynamic profiles of TRAIL (Kim, et al., *Bioconjugate Chem.*, 22 (8), pp 1631-1637 (2011)). Studies show that TRAIL analogues derivatized with PEG maintain anti-cancer activity, while also exhibiting higher metabolic stabilities in plasma, extended pharmacokinetic profiles, and greater circulating half-lives (Chae, et al., *Molecular cancer therapeutics* 9(6): 1719-29 (2010); Kim, et al., *Bioconjugate chemistry*, 22(8): 1631-7 (2011); Kim, et al., *Journal of pharmaceutical sciences* 100(2):482-91 (2011); Kim, et al., *Journal of controlled release: official journal of the Controlled Release Society* 150(1):639 (2011)).

Therefore, in some embodiments, the TRAIL domain is derivatized with one or more ethylene glycol (EG) units, more preferably 2 or more EG units (i.e., polyethylene glycol (PEG)), or a derivative thereof. Derivatives of PEG include, but are not limited to, methoxypolyethylene glycol succinimidyl propionate, methoxypolyethylene glycol N-hydroxysuccinimide, methoxypolyethylene glycol aldehyde, methoxypolyethylene glycol maleimide and multiple-branched polyethylene glycol.

The precise number of EG or derivative units depends on the desired activity, plasma stability, and pharmacokinetic profile. For example, Kim, et al. (supra) reported that 2, 5, 10, 20, and 30K-PEG-TRAIL resulted in greater circulating half-lives of 3.9, 5.3, 6.2, 12.3, and 17.7 h respectively in mice, versus 1.1 h for TRAIL. In some embodiments, the molecular weight of the PEG is between about 1 and 100 kDa, preferably between about 1 and 50 kDa. For example, the PEG can have a molecular weight of "N" kDa, wherein N is any integer between 1 and 100. The PEG can have a molecular weight of "N" Da, wherein N is any integer between 1.000 and 1,000,000. In a particular embodiment, the molecular weight of the PEG is "N" Da, wherein "N" is between 1,000 and 50,000, or more preferably between 5,000 and 50,000.

The pro-apoptotic agent can be conjugated with linear or branched PEG. Some studies have shown that proteins derivatized with branched PEG have extended in vivo circulation half-lives compared to linear PEG-proteins, thought to be due partly to a greater hydrodynamic volume of branched PEG-proteins Fee, et al., *Biotechnol Bioeng.*, 98(4):725-3 (2007).

Peptide ligands can be derivatized at the C-terminus, or preferably at the N-terminus, using methods that are known in the art.

The TRAIL-PEG conjugates may be depicted by the following formula:

$$X\text{-}L\text{-}(PEG)_n,$$

wherein
X represents a TRAIL protein,
L represents a linker,
PEG represents a branched poly(ethylene glycol) chain, and
n is an integer selected from 2, 3, 4, 5, 6, 7 or 8.
In certain embodiments, n is 2.

The polyalkylene oxide is coupled to the protein via a linker. The linker may be a polyakylene oxide, and preferably connects two polyalkylene oxide polymers to the protein.

In a particular embodiment, the TRAIL-conjugate is a PEG-conjugate that includes a TRAIL domain including a truncated form of human TRAIL, for example, from arginine-114 to glycine-281 of the full-length form (1-281) of human TRAIL, and PEG having a molecular weight between 1,000 and 100,000 Daltons, and preferably between 5,000 and 50,000 Daltons.

N-terminal modified PEG-TRAIL conjugates can be obtained by reacting an N-terminal amine of the TRAIL domain with an aldehyde group of the PEG in the presence of a reducing agent. PEG and TRAIL can be reacted at a molar ratio (PEG/TRAIL) of 2 to 10, or preferably 5 to 7.5.

In preferred embodiments, the TRAIL-conjugate includes a zipper amino acid motif, for example, an isoleucine zipper motif, that allows for trimer formation between three TRAIL-conjugate monomers.

The PEG chains are preferably, but not necessarily, of equal molecular weight. Exemplary molecular weight ranges for each PEG chain is between about 10 kDa and 60 kDa, and preferably about 20 kDa and 40 kDa. PEG40 is a branched PEG moiety was synthesized and has a molecular weight of 40 kDa: 20+20 kDa (each PEG chain).

A trimeric PEG moiety can consist of a branched PEG chain attached to a linker arm.

A visual description of the trimer PEG moiety is provided immediately below.

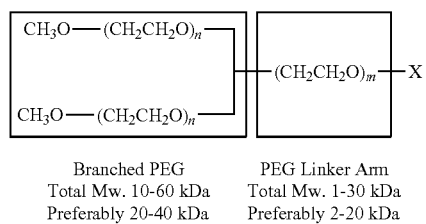

Branched PEG
Total Mw. 10-60 kDa
Preferably 20-40 kDa

PEG Linker Arm
Total Mw. 1-30 kDa
Preferably 2-20 kDa

The following trimeric PEGs were synthesized: YPEG42, YPEG43.5, YPEG45, YPEG50 and YPEG60.
  YPEG42 is a trimeric PEG moiety which has a molecular weight of 42 kDa: (20+20 kDa) (branched PEG)+2 kDa (linker arm).
  YPEG43.5 is a trimeric PEG moiety which has a molecular weight of 43.5 kDa: (20+20 kDa) (branched PEG)+ 3.5 kDa (linker arm).
  YPEG45 is a trimeric PEG moiety which has a molecular weight of 45 kDa: (20+20 kDa) (branched PEG)+5 kDa (linker arm).
  YPEG50 is a trimeric PEG moiety which has a molecular weight of 50 kDa: (20+20 kDa) (branched PEG)+10 kDa (linker arm).
  YPEG60 is a trimeric PEG moiety which has a molecular weight of 60 kDa: (20+20 kDa) (branched PEG)+20 kDa (linker arm).

ii. Linker Moiety

The protein or peptide is covalently joined to the branched PEG moiety via a linker. The linker is a polymer, and generally has an atomic length of at least 800 angstroms. Typically, the linker has an atomic length from about 800 to about 2,000 angstrom, from about 800 to about 1,500 angstrom, from about 800 to about 1,000 angstrom, or from about 900 to about 1,000 angstrom. It is to be appreciated that the atomic distances listed above refer to fully extended polymers, and that when in the solid state or solution the linker may fold or curl in ways such that the actual distance between the branched PEG and protein or peptide is less than the atomic lengths listed above.

In certain embodiments, the linker is a poly(ethylene glycol) derivative with a molecular weight between about 1 kDa to 30 kDa, preferably from about 2 kDa to 20 kDa. A linker may also be a natural or unnatural amino acid of at least 80 units in length.

PEG alternatives for the linker include synthetic or natural water-soluble biocompatible polymers such as polyethylene oxide, polyvinyl alcohol, polyacrylamide, proteins such as hyaluronic acid and chondroitin sulfate, celluloses such as hydroxymethyl cellulose, polyvinyl alcohol, and polyhydroxyalkyl (meth)acrylates.

Proteins and peptides may be covalently bound to the linker using conventional chemistries. Primary amine groups, such as found at the N-terminus or in lysine residues, will react with aldehydes and their equivalents under reductive conditions to give amines. (Molineux, *Current pharmaceutical design*, 10(11):1235-1244 (2004)). Mercapto (—SH) groups, such as found in cysteine residues, can undergo a conjugate addition with a variety of Michael acceptors, including acrylic and methacrylic acid derivatives, as well as maleimides (Gong et al., *British Journal of Pharmacology*, 163(2):399-412 (2011)). Other suitable nucleophilic groups found in peptides and proteins include disulfide bonds (Brocchini, et al., *Nature protocols*, 1:2241-2252 (2006)) and histidine residues (Cong, et al., *Bioconjugate Chemistry*, 23(2):248-263 (2012)).

The linker may be covalently joined to the protein or peptide using conventional chemistries. For instance, the linker polymer may be derivatized at one end with an electrophilic group such as an aldehyde, epoxide, halogen (chlorine, bromide, iodine), sulfonate ester (tosylate, mesylate), Michael acceptor, or activated carboxylates and then reacted with a nucleophilic amine or thiol group in the protein or peptide. Suitable Michael acceptors include acylic and methacrylic acid derivatives such as acrylamides, methacrylamides, acrylates and methacrylates, as well as maleimides. Suitable activated carboxylates include nitrophenyl carbonate and NHS (N-hydroxy succinate) esters. In other embodiments, peptides and proteins containing arginine residues may be covalently joined with a linker containing a reactive 1,3 diketone functional group.

The conjugates may be prepared by first joining the linker with the peptide or protein, followed by joining the linker with the branched poly(ethylene glycol), or by first joining the linker with the branched poly(ethylene glycol), followed by joining the linker with the peptide or protein. The optimal sequence of bond formation is determined by the specific chemical transformations involved.

c. Macromolecules

In other embodiments, TRAIL can be derivatized as a long-acting TRAIL with an extended half-life using biopolymers or polypeptides through reported methods; for example, but not limited to, using chemically conjugated hyaluronic acid (Yang et al., *Biomaterials* 32(33); 8722-8729 (2011), depot forming polypeptides (Amiram et al., *Proc Natl Acad Sci USA*, 110(8):27922792 (2013). U.S. Published Application No. US 2013-0178416 A1) and TRAIL linked to extended recombinant polypeptides (U.S. Published Application No. US 2010-0239554 A1).

d. Complexes

The TRAIL domain can be complexed with a negatively charged moiety. In some embodiments the negatively charged moiety can facilitate loading of the ligand or agonist into a nanoparticle for extended, sustained, or time released delivery. In some embodiments, the negatively charged moiety itself mediates extended, sustained, or time released delivery of the ligand or agonist. Preferably, the negatively charged moiety does not substantially reduce the ability of the ligand or agonist to induce or enhance apoptosis.

The formation of a complex between positively charged TRAIL and the negatively charged chondroitin sulfate (CS) (CS/TRAIL) was developed and shown to facilitate loading of TRAIL in poly(lactide-co-glycolide) (PLGA) microspheres (MSs), without compromising the activity of the TRAIL (Kim, et al., *Journal of Pharmacy and Pharmacology,* 65(1):11-21 (2013). A nanocomplex of approximately 200 nm was formed in a weight ratio of 2 TRAIL to CS (TC2) at pH 5.0. The complex had >95% higher loading efficiency in PLGA MSs prepared by the multi-emulsion method than that of native TRAIL. Therefore, in some embodiments, the ligand or agonist, particularly TRAIL peptides, and variants, functional fragments and fusion proteins thereof, or conjugates thereof such as PEG-conjugates are complexed with chondroitin sulfate and optionally loaded into micro- or nanoparticles, for example, PLGA-based particles.

In other embodiments, the ligand or agonist, particularly TRAIL peptides, and variants, functional fragments and fusion proteins thereof, or conjugates thereof such as PEG-conjugates are complexed with hyaluronic acid (HA). Nanocomplexes of PEG-TRAIL and HA prepared by mixing positively charged PEG-TRAIL and negatively charged HA, were shown to have sustained delivery in vivo, with negligible loss of bioactivity compared with the PEGTRAIL (Kim, et al., *Biomaterials,* 31(34):9057-64 (2010)). Delivery was further enhanced by administering the nanoparticles in a 1% HA containing solution.

B. Antibody Composition and Methods of Manufacture

Purified TRAIL receptor polypeptides, fragments, fusions, or antigens or epitopes thereof can be used to prepare an antibody that specifically binds to a TRAIL receptor. Antibodies can be prepared using any suitable methods known in the art. Subsequently, the antibodies can be screened for functional activity (e.g., agonistic or antagonistic activity) using methods known in the art. Exemplary agonistic antibodies include antibodies to death receptors DR4 and DR5.

1. Death Receptor Agonistic Antibodies

Certain aspects of the disclosure include agonistic antibodies (including, or alternatively, antibody fragments or variants thereof) directed towards death receptors (e.g., TRAIL antibodies). Antibodies can be made and purified using methods known to those skilled in the art. For example, an antibody can be affinity purified from the serum of an animal (e.g., a mouse, rat, rabbit, goat, donkey, horse, duck, or chicken). A variety of available DR antibodies, DR4 and DR5 antibodies, can also be used for the treatment of fibrotic autoimmune disease (e.g., systemic sclerosis). Exemplary DR agonists include Lexatumumab, Tigatuzumab, Conatumumab, Drozitumab, Mapatumumab, HGSTR2J/KMTRS, and LBY-135. In some embodiments, DR antibody is a multivalent agent, e.g. TAS266.

An antibody of the disclosure may refer to a polypeptide that includes canonical immunoglobulin sequence elements sufficient to confer specific binding to a particular target antigen. As is known in the art, intact antibodies as produced in nature are approximately 150 kD tetrameric agents of two identical heavy chain polypeptides (about 50 kD each) and two identical light chain polypeptides (about 25 kD each) that associate with each other into what is commonly referred to as a "Y-shaped" structure. Each heavy chain includes at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain includes two domains—an amino-terminal variable (VL) domain, followed by a carboxy-terminal constant (CL) domain, separated from one another by another "switch". Intact antibody tetramers are composed of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are fully human, or are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation.

Antibodies can be generated in cell culture, in phage, or in various animals. In one embodiment, an antibody is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles And Practice* (Academic Press, 1993); *Current Protocols In Immunology* (John Wiley & Sons, most recent edition).

The disclosed antibodies can be modified by recombinant means to increase greater efficacy of the antibody in mediating the desired function. Antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, WO 9958572; and Angal, et al., *Mol. Immunol.* 30:105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to TRAIL receptors. See e.g., *Antibody Engineering: A Practical Approach* (Oxford University Press, 1996).

Suitable antibodies with the desired biologic activities can be identified by in vitro assays including but not limited to: proliferation, migration, adhesion, soft agar growth, angiogenesis, cell-cell communication, apoptosis, transport, signal transduction, and the following in vivo assays such as the inhibition of tumor growth.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A monoclonal antibody is obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

Antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

2. Human and Humanized Antibodies

Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge. Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from nonhuman immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances. Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a non-human antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies are preferably prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way. FR residues can be selected and combined from the consensus and import sequence so that the desired antibody characteristic, such as increased affinity for the target antigen(s), is achieved. In general, the CDR residues are directly and most substantially involved in influencing antigen binding.

3. Single-Chain Antibodies

Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

4. Monovalent Antibodies

In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the F(ab')2 fragment that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

5. Hybrid Antibodies

The antibodies can be a hybrid antibody. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., a bivalent antibody has the ability to bind at least two different epitopes simultaneously. Such hybrids can be formed by fusion of hybridomas producing the respective component antibodies, or by recombinant techniques. Such hybrids may, of course, also be formed using chimeric chains.

6. Method of Making Antibodies Using Protein Chemistry

One method of producing proteins comprising the antibodies is to link two or more peptides or polypeptides together by protein chemistry techniques. For example, peptides or polypeptides can be chemically synthesized using currently available laboratory equipment using either Fmoc (9fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo as described above. Once isolated, these independent peptides or polypeptides may be linked to form an antibody or antigen binding fragment thereof via similar peptide condensation reactions.

For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method consists of a two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

III. Methods of Use

The death receptor agonists disclosed herein may be used alone, or as active agents in pharmaceutical compositions or formulation, for treating subjects with autoimmune fibrosis, such as systemic sclerosis.

A. Scleroderma (Systemic Sclerosis, SSc)

Scleroderma is an autoimmune, rheumatic, and chronic disease that affects the body by hardening of the connective tissue. Connective tissue is made of many kinds of proteins (e.g., collagen), and is widespread. SSc causes fibrosis of the skin and internal organs, and is a lethal component of SSc.

Fibrosis is a pathological process characterized by excessive accumulation of connective tissue components in an organ or tissue. Fibrosis is produced by deregulated wound healing (e.g., excess collagen production) in response to chronic tissue injury or chronic inflammation. The excess of collagen prevents organs from functioning normally (JHU Scleroderma Center). Progressive fibrosis, which distorts tissue architecture and results in progressive loss of organ function, is recognized as one of the major causes of morbidity and mortality in individuals with SSc (one of the most lethal rheumatic diseases). Activated alpha smooth muscle actin ($\alpha$-SMA) myofibroblasts are cells that produce the extracellular matrix scar in fibrosis (Ho et al., *Nat Rev Rheumatol* 10, 390-402 (2014)). $\alpha$-SMA$^+$ cells are often used as a biomarker for myofibroblasts formation, and are the significant originators of scleroderma.

SSc is a rare disease, and fewer than 500,000 people in the United States are currently diagnosed. Approximately 80% of patients are women, and the average age of diagnosis is in the 40s (between 35 and 50). Death results most often from pulmonary, heart and kidney involvement, although survival has greatly improved with effective treatment for kidney failure. Lung fibrosis is the most common cause of death with a 50% mortality rate within 10 years of diagnosis.

Early symptoms of SSc include changes in fingers, wherein they become very sensitive to cold and can change color with cold or emotional stress (e.g., Raynaud's phenomenon), and can become stiff and swollen. Finger color changes are caused by spasm and narrowing of blood vessels. This occurs because of excess collagen that has narrowed the blood vessels and over reaction of the skin blood vessel to cold temperatures and emotional stress. The cold sensitivity and color changes are called Raynaud's phenomenon. Raynaud's phenomenon is a common condition. Most people with Raynaud's phenomenon will not develop scleroderma. There are two types of Raynaud's phenomenon: primary (a subject who is diagnosed with Raynaud's phenomenon and not with scleroderma), and secondary (a subject who is diagnosed with both Raynaud's phenomenon and scleroderma).

Fibrosis can also affect internal organs and can lead to impairment or failure of the affected organs. The most commonly affected organs are the esophagus, heart, lungs, and kidneys. Internal organ involvement may be signaled by heartburn, difficulty swallowing (dysphagia), high blood pressure (hypertension), kidney problems, shortness of breath, diarrhea, or impairment of the muscle contractions that move foxod through the digestive tract.

Approximately 15 percent to 25 percent of people with features of systemic scleroderma also have signs and symptoms of another condition that affects connective tissue, such as polymyositis, dermatomyositis, rheumatoid arthritis, Sjögren syndrome, or systemic lupus erythematosus. The combination of systemic scleroderma with other connective tissue abnormalities is known as scleroderma overlap syndrome.

1. Types of Scleroderma a. Limited Scleroderma (CREST Syndrome)

Limited scleroderma is characterized as a more mild form of SSc. Limited scleroderma mostly affects the skin of the face neck and distal elbows and knees, and late in the disease causes isolated pulmonary hypertension. Generally, limited scleroderma causes less involvement of body organs than the more severe form. Some patients can develop lung and heart disease.

Limited scleroderma is associated with CREST (Calcinosis, Raynaud's phenomenon, Esophageal dysfunction, Sclerodactyly, Telangiectasis) syndrome. Calcium in the skin and tissues can be painful and can irritate or break the skin surface. As described above. Raynaud's syndrome is associated with cold intolerance. Acid reflux from esophageal dysmotility can be painful causing irritation in the lining of the esophagus. Telangiectasia is a condition characterized by dilation of the capillaries and causes them to appear as red or purple clusters. They typically do not cause symptoms, and can be removed by laser therapy.

b. Diffuse Scleroderma

Diffuse scleroderma often affects more areas including skin, heart, lungs, GI tract and kidneys (e.g., the areas become thickened by overproduction of collagen). Tightened skin makes bending fingers, hands and other joints more difficult, and often inflammation of the joints, tendons and muscles is observed.

c. Systemic Sclerosis Sine Scleroderma

In systemic sclerosis sine scleroderma, fibrosis affects one or more internal organs but not the skin. The affected internal organs include esophagus, lungs, heart and kidney.

B. Subjects to be Treated

Subjects to be treated with the disclosed methods include patients suffering from systemic sclerosis. The patients may be suffering from limited scleroderma or diffuse scleroderma. The patient may be suffering from early symptoms of SSc and may have Raynaud's primary or secondary phenomenon. The patients may be suffering from calcinosis, Raynaud's phenomenon, esophageal dysfunction, sclerodactyly, telangiectasis and/or diffuse scleroderma. The patient may be an early, middle, or advanced stages of the disease.

Subjects to be treated may be suffering from one or more forms of systemic sclerosis in the absence of other fibrotic diseases, such as fibrosis or inflammation of internal organs. Examples include patient populations who suffer from systemic sclerosis in the presence or absence of liver fibrosis, subjects suffering from systemic sclerosis in the presence or absence of liver cirrhosis, subjects suffering from systemic scleroderma in the presence or absence of pancreatic fibrosis, and subjects suffering from systemic sclerosis in the presence or absence of pancreatitis.

Other examples of subjects to be treated include patients who suffer from systemic sclerosis in the presence or absence of type 2 diabetes, arthritis, or other autoimmune diseases, such as type 1 diabetes, rheumatoid arthritis, systemic lupus erythematosus, or multiple sclerosis.

Other examples of subjects to be treated include patients who suffer from systemic sclerosis in the presence or absence of a proliferative disease, such as cancer.

C. Current Therapies and Treatment for SSc

Currently, there is no cure for SSc; however, treatment is available for some of the symptoms. Exemplary such treatments include drugs to soften the skin and reduce inflammation, additionally patient exposure to heat has been demonstrated to have beneficial effects. Although there are no effective and safe long-term therapies or FDA approved drugs, topical treatments are available that do not alter the progression of the disease, but may improve symptoms (e.g., pain and ulceration). Immunosuppressive drugs can be used, although glucocorticoids have limited application. A variety of nonsteroidal ant-inflammatory drugs (NSAIDs) can also be used (e.g., naproxen), as well as steroids (e.g., prednisone). Other agents that are helpful in relief of symptoms include calcium channel blockers (e.g., nifedipine), prostacyclin, endothelin-receptor agonist (e.g., bosentan), methotrexate, ciclosporin, penicillamine, ACE inhibitors, cyclophosphamide, epoprostenol, bosentan and aerolized iloprost.

Research within the pharmaceutical industry is often directed towards idiopathic pulmonary fibrosis (IPF) in conjunction with scleroderma. The pipeline of research at several pharmaceutical companies, including Hoffmann-La Roche, Ltd, Bayer AG, Celgene Corporation, InterMune, Inc. and Corbus Pharmaceuticals Holdings, Inc. is associated with autoimmune diseases (e.g., rheumatoid arthritis and juvenile idiopathic arthritis). None of the current therapeutic strategies, however, focus on reversing fibrosis and resolving inflammation with respect to SSc.

D. Combination Therapies

Combination therapies include administering to a subject an effective amount of a death receptor agonist together with one or more additional agents. Additional agents may include therapeutics currently used for ameliorating the symptoms of systemic sclerosis.

Additional agents include immunosuppressive drugs such as methotrexate, azathioprine, mercaptopurine, dactinomycin, anthracyclines, mitomycin C, bleomycin, mithramycin, glucocorticoids, basiliximab, daclizumab, muromonab-CD3, ciclosporin, tacrolimus, sirolimus, everolimus, interferons, and mycophenolate, antimicrobial agents such as neomycin, streptomycin, chloramphenicol, cephalosporin, ampicillin, penicillin, tetracycline, and ciprofloxacin, steroids and steroidal drugs as clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate, non-steroidal anti-inflammatory drugs such as indomethacin, ketoprofen, flurbiprofen, naproxen, ibuprofen, ramifenazone, and piroxicam, analgesics such as aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate, vitamins, calcium channel blockers such as amlodipinen, diltiazem, felodipine, isradipine, nicardipine, nifedipine, nisoldipine, and verapamil, endothelin-receptor agonists, methotrexate, ciclosporin, penicillamine, ACE inhibitors such as benazepril captopril, enalapril, fosinopril, lisinopril, moexipril, perindopril, quinapril, ramipril, and trandolapril, cyclophosphamide, epoprostenol, bosentan and aerolized iloprost.

The additional agents may be administered simultaneously with the death receptor agonists.

Alternatively, the additional agents may be administered prior to, or subsequent to administering an effective amount of a death receptor agonist. Prior to, or subsequent administration of the additional agent(s) may be separated in time from the administration of the effective amount of a death receptor agonist by at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks, or at least a month.

E. Pharmaceutical Compositions and Dosage Regimes

1. Pharmaceutical Compositions

Another aspect of the disclosure pertains to pharmaceutical compositions of the compounds. The pharmaceutical compositions of the disclosure typically include an agent, such as a death receptor agonist, and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active agent, use thereof in the pharmaceutical compositions is contemplated. Supplementary active agents can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the agents can be administered in a time release formulation, for example in a composition which includes a slow release polymer. The active agents can be prepared with carriers that will protect the agent against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active agent in the required amount in an appropriate solvent with one or a combination of ingredients enumerated above, as required, followed by filtered sterilization. Generally, dispersions are prepared by incorporating the agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Depending on the route of administration, the agent may be coated in a material to protect it from the action of enzymes, acids and other natural conditions which may inactivate the agent. For example, the agent can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes (Strejan, et al., (1984) J. Neuroimmunol 7:27). Dispersions can also be prepared in glycerol, liquid polyethylene glycols, and mixtures thereof and in oils. Under ordinary conditions of storage and use, these preparations may contain a preservative to prevent the growth of microorganisms.

2. Effective Amounts and Dosage Unit Forms

The active agent in the composition (e.g., $TRAIL_{PEG}$, DR antibody) preferably is formulated in the composition in a therapeutically effective amount. A therapeutically effective amount of an active agent may vary according to factors such as the disease state, age, sex, and weight of the individual, and the ability of the agent to elicit a desired response in the individual. Dosage regimens may be adjusted to provide a beneficial therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic effect to be achieved, and (b) the limitations inherent in the art of compounding such an active compound for the treatment of sensitivity in individuals.

3. Dosages and Routes of Administration

Exemplary dosages of agents (e.g. $TRAIL_{PEG}$, DR antibody) include e.g., between about 0.0001% and 5%, about 0.0001% and 1%, about 0.0001% and 0.1%, about 0.001% and 0.1%, about 0.005% and 0.1%, about 0.01% and 0.1%, about 0.01% and 0.05% and about 0.05% and 0.1%. Optionally, doses include between about 0.001% and about 50%, about 0.01% and about 5%, about 0.1% and about 2.5%, about 0.2% and about 2%, about 0.3% and about 1.5%, about 0.4% and about 1.25%, about 0.5% and about 1%, about 0.6% and about 0.9% and about 0.7% and about 0.8% of a pharmaceutical composition or formulation. Exemplary dosages can also be expressed in proportion to the weight of a treated subject, e.g., in mg/kg, such as between about 0.0001 mg/kg and about 1 g/kg, 0.001 mg/kg and about 1 g/kg, about 0.01 mg/kg and about 1 g/kg, about 0.1 mg/kg and about 1 g/kg, about 0.2 mg/kg and about 500 mg/kg, 0.3 mg/kg and about 200 mg/kg, about 0.4 mg/kg and about 100 mg/kg, about 0.5 mg/kg and about 50 mg/kg, about 0.6 mg/kg and about 30 mg/kg, about 0.7 mg/kg and about 20 mg/kg, about 0.8 mg/kg and about 15 mg/kg, about 1 mg/kg and about 10 mg/kg, about 2 mg/kg and about 8 mg/kg and about 4 mg/kg and about 6 mg/kg.

The death receptor agonist may be administered systemically, enterally, parenterally, locally, or via buccal delivery. Optionally, the death receptor agonist is administered locally. Local administration includes topical and/or subcutaneous administration. The effective amount of the agonist(s) may be administered in a single administration, or in one or more administrations.

The agent(s) (death receptor agonist(s)) may be administered at an effective dose in one or more administrations. Each administration of an effective dose of the agent(s) may be separated in Lime by at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks, or at least a month.

The agent(s) can be administered in a manner that prolongs the duration of the bioavailability of the compound(s), increases the duration of action of the agent(s) and the release time frame of the agent by an amount selected from the group consisting of at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks, and at least a month, but at least some amount over that of the agent(s) in the absence of composition provided herein. Optionally, the duration of any or all of the preceding effects is extended by at least 30 minutes, at least an hour, at least 2 hours, at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks or at least a month.

An agent can be formulated into a pharmaceutical composition wherein the agent is the only active agent therein. Alternatively, the pharmaceutical composition can contain additional active agents. For example, two or more compounds may be used in combination. Moreover, a compound can be combined with one or more other agents that have modulatory effects on an autoimmune disease (e.g. systemic sclerosis).

IV. Kits

The disclosure also includes kits that include an effective amount of an agent, such as death receptor agonist (e.g. $TRAIL_{PEG}$ and DR antibody), and instructions for use.

The kits may include effective dosages of the agents in one or more sterilized, pre-packaged syringes, capsules, tablets, powders, gels, or patches ready for administration.

The kits may include additional agents together with the effective dosages of the agents for combination therapies.

The present invention will be further understood by reference to the following non-limiting examples.

This invention is further illustrated by the following examples which should not be construed as limiting. The contents of all references, patents, and published patent applications cited throughout this application, as well as the figures, are incorporated herein by reference.

EXAMPLES

Example 1: Activated Fibroblasts Upregulate Death Receptors (DRs) and Agonists of DR Selectively Induce Apoptosis in Activated Myofibroblasts but not Normal Fibroblasts Activated, α-SMA$^+$ fibroblasts (myofibroblasts) are one of the originators of scleroderma. It was herein identified that selective eradication of myofibroblasts in vivo reversed SSc and resolved inflammation. To date, no clinically tested robust methods have existed to target and affect myofibroblasts in humans. $TRAIL_{PEG}$ was previously identified to have reversed severe fibrosis in the liver and pancreas by targeting α-SMA$^+$ activated hepatic and pancreatic stellate cells (International Application Publication No. WO/2015/164217). In this disclosure, TRAIL, $TRAIL_{PEG}$ and DR5 antibody were identified to have targeted α-SMA$^+$ myofibroblasts transformed from fibroblasts and simultaneously inhibited multiple key factors in SSc. When primary healthy dermal fibroblasts were activated by TGF-β1 for 54 hrs, activated fibroblasts upregulated the mRNA and protein levels of α-SMA, DR4, DR5 and fibrotic markers including collagen (Tables 1 and 2). Importantly, when activated fibroblasts are treated with recombinant TRAIL (R&D Systems™, 1 ug/mL), $TRAIL_{PEG}$ (1 ug/mL) and DR5 antibodies (1 ug/mL, Conatumumab with protein G and HGSTR2J/KMTRS) for 3 hrs in vitro, only activated myofibroblasts showed increased levels of apoptotic markers, active caspase-8 and caspase-3/7 and display morphological changes due to TRAIL-induced apoptosis (Table 3). Primary human lung fibroblasts (ATCC® CCL-151) were also activated by TGF-β1 (10 ng/mL) for 54 hours and then treated with $TRAIL_{PEG}$, and only activated lung fibroblasts display morphological changes due to TRAIL-induced apoptosis. The following examples provided herein support $TRAIL_{PEG}$ and DR antibody efficacies in scleroderma models, e.g., skin and pulmonary fibrosis.

TABLE 1

_mRNA levels (relative fold) of death receptors, α-SMA (ACTA2) and collagen in normal and TGF-β1 activated human primary dermal fibroblasts.

| Gene | Normal Fibroblasts | TGF-β1 activated fibroblasts |
| --- | --- | --- |
| DR4 | 1.0 ± 0.1 | 9.2 ± 1.9*** |
| DR5 | 1.0 ± 0.1 | 8.5 ± 1.3*** |
| ACTA2 | 1.0 ± 0.1 | 4.1 ± 0.7*** |
| Col1A2 | 1.0 ± 0.1 | 9.2 ± 4.9*** |

***P < 0.001 vs. normal fibroblasts.

TABLE 2

_Protein levels (relative fold) of death receptors and α-SMA in normal and TGF-β1 activated human primary dermal fibroblasts.

| Protein | Normal Fibroblasts | TGF-β1 activated fibroblasts |
| --- | --- | --- |
| DR4 | 1.0 ± 0.1 | 2.9 ± 0.1*** |
| DR5 | 1.0 ± 0.2 | 5.1 ± 0.9** |
| α-SMA | 1.0 ± 0.1 | 1.9 ± 0.1*** |

**P < 0.01,
***p < 0.001 vs. normal fibroblasts.

TABLE 3

Casepse-3/7 (apoptosis marker) activities (relative fold) in normal fibroblasts (normal) and TGF-β1 activated human primary dermal fibroblasts (MFB) treated with TRAIL, TRAIL$_{PEG}$ and DR5 antibodies (Conatumumab with protein G and HGSTR2J/KMTRS).

| Activity | Normal + PBS | Normal + TRAIL$_{PEG}$ | MFB + PBS | MFB + TRAIL | MFB + TRAIL$_{PEG}$ | MFB + Conatumumab | MFB + KMTRS |
|---|---|---|---|---|---|---|---|
| Caspase-3/7 | 1.0 ± 0.1 | 1.3 ± 0.1 | 1.2 ± 0.1 | 20.0 ± 1.5*** | 28.0 ± 0.7*** | 25.0 ± 2.5*** | 30.0 ± 3.5*** |

***$P < 0.001$ vs. normal fibroblasts.

Example 2: TRAIL$_{PEG}$ Reversed Skin Thickening and Collagen Deposition

Study Design I (Mild Fibrosis in Bleomycin-Induced SSc Mouse Models)

For in vivo studies, a mouse model using bleomycin-induced scleroderma was used. Mice (DBA2/J) were treated with subcutaneous (s.c.) bleomycin (day 0-28). TRAIL$_{PEG}$ (10, 20 mg/kg) or phosphate buffered saline (PBS) were intraperitoneally (i.p.) treated every other day for two weeks from day 15; n=5 per group. A schematic of the experimental design is depicted in FIG. 1. Tissue samples from skin and lung were collected on Day 28 of the model and prepared for histology by formalin treatment. Paraffin-embedded tissue sections were stained with hematoxylin-eosin (H&E). Also, tissue sections were analyzed for a number of fibrogenic markers (collagen, cz-SMA) using immunohistochemistry. Tissue homogenates were analyzed by western blot and RT-PCT for fibrogenic markers as well.

Figure 2:
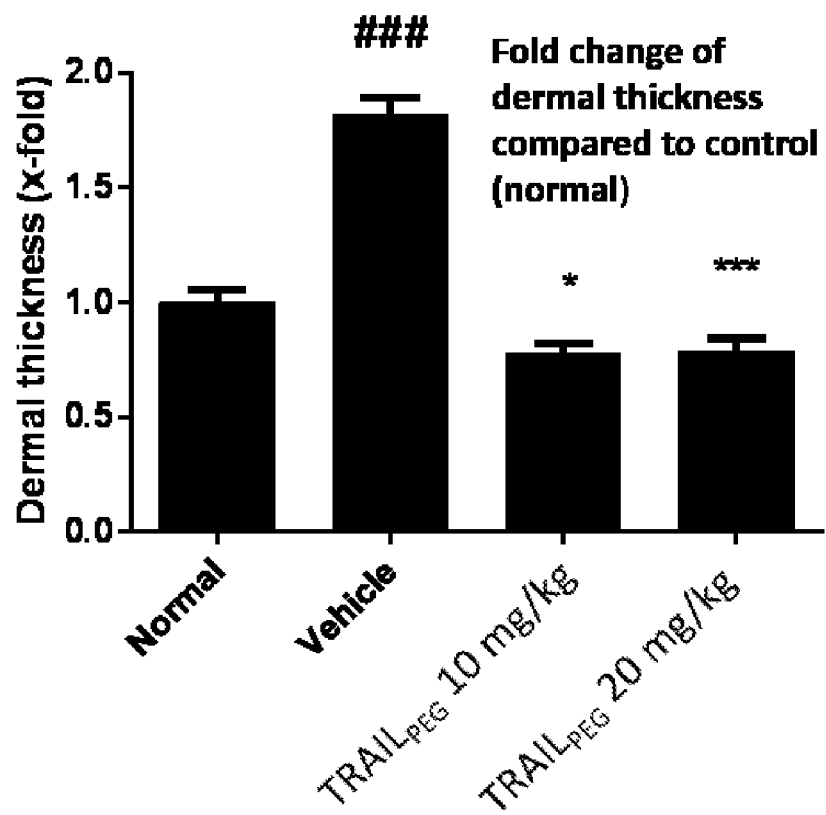
FIG. 2 depicts a bar graph showing the quantitative evaluation of dermal thickness. Dermal thickness of the dermis was increased greater than 70% in bleomycin-induced skin fibrosis compared with healthy skin. TRAIL$_{PEG}$ attenuated the increase in dermal thickness and returned it back to normal levels. $^{\#\#\#\#}P<0.001$ vs. Normal, *P<0.05 vs. Vehicle, ***P<0.001 vs. Vehicle.

TRAIL$_{PEG}$ Treatment Reversed Skin Thickening to Near Normal Stages after 2 Week Treatment in Mouse Skin Scleroderma Model To evaluate the effects of TRAIL$_{PEG}$ in a mouse model of scleroderma, a bleomycin induced dermal fibrosis model was used. To assess the treatment of established fibrosis, injections of TRAIL$_{PEG}$ treatment were initiated 2 weeks after the onset of bleomycin injections. After TRAIL$_{PEG}$ treatment for 2 weeks, inflammatory cell infiltration was reduced in TRAIL$_{PEG}$ treated mice. Quantitative evaluation showed that thickness of the dermis was increased by greater than 70% in bleomycin-induced skin fibrosis model mice, as compared with healthy skin; however, administration of TRAIL$_{PEG}$ to such mice attenuated the increase in dermal thickness and returned it back to normal levels (FIG. 2).

TRAIL$_{PEG}$ Treatment Reduced Collagen Depositions to Near Normal Stages after 2 Week Treatment in Mouse Skin Scleroderma Model Skin lesions in bleomycin-induced fibrosis showed dense accumulation of thick collagen bundles in the dermis, reflecting increased collagen deposition. However, the mice given TRAIL$_{PEG}$ with continued bleomycin insult showed significantly reduced collagen deposition. The sections were subjected to trichrome stain, which permitted the areas of mature collagen deposition to be detected. Skin lesions in bleomycin induced mice showed dense accumulation of thick collagen bundles in the dermis, reflecting increased collagen deposition. However, mice given TRAIL$_{PEG}$ together with bleomycin showed significantly reversed collagen deposition.

Figure 3:
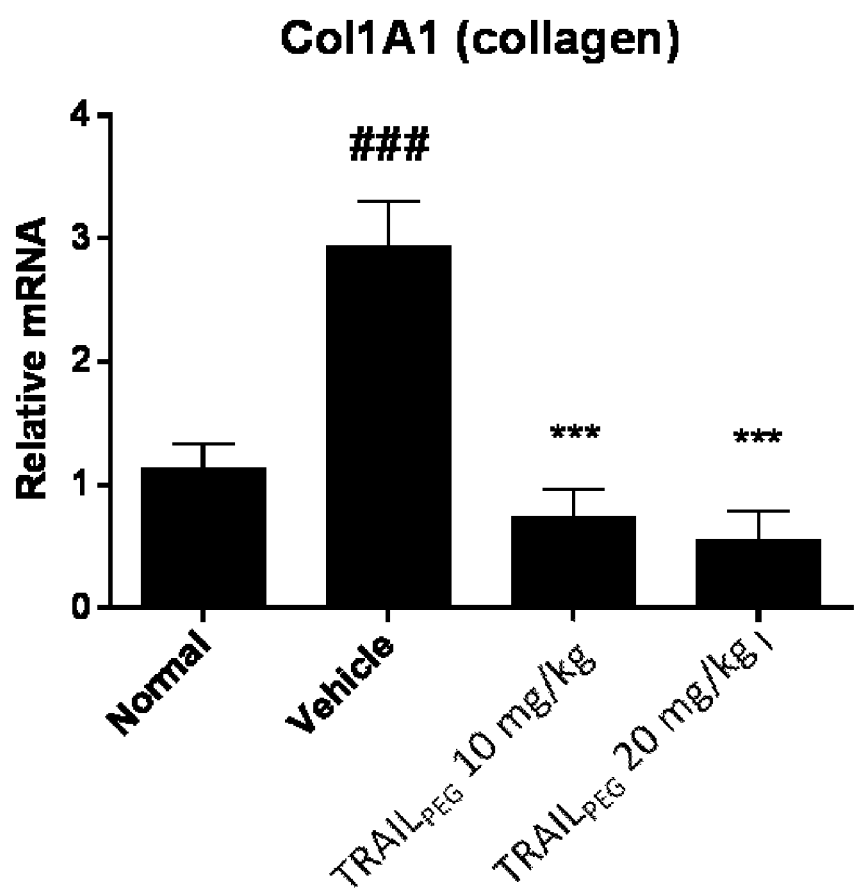
FIG. 3 depicts a bar graph showing Col1A1 mRNA expression in the lesional skin which was quantified by real-time PCR. A 3-fold increase in the levels of Col1A1 and Col1A2 mRNA in mice treated with bleomycin compared with normal mice were observed. TRAIL$_{PEG}$ treatment markedly attenuated the up-regulation of collagen mRNA. $^{\#\#\#\#}P<0.001$ vs. Normal, ***P<0.001 vs. Vehicle.

To examine the effects of TRAIL$_{PEG}$ on collagen gene expression in vivo, mRNA in the lesional skin was quantified by real-time PCR. The results showed a 3-fold increase in the levels of Col1A1 and Col1A2 mRNA in mice treated with bleomycin, as compared with normal mice. TRAIL$_{PEG}$ treatment markedly down-regulated collagen mRNA (FIG. 3).

Example 3: TRAIL$_{PEG}$ Targeted the Originator of SSc

TRAIL$_{PEG}$ Treatment Significantly Down-Regulated α-SMA$^+$ Cell Populations (e.g. Activated Fibroblasts, Myofibroblasts—the Originator of SSc)

The expression of α-SMA, a marker for identifying myofibroblasts that play crucial roles in pathological fibrogenesis, was determined by immunohistochemistry. In bleomycin treated mice, increased α-SMA was noted in the lesional dermis and subcutaneous layers. TRAIL$_{PEG}$ treatment significantly reduced the number of α-SMA$^+$ fibroblastic cells. In bleomycin treated mice, increased α-SMA was noted in the lesional dermis and subcutaneous layers. TRAIL$_{PEG}$ treatment significantly reduced the number of α-SMA$^+$ fibroblastic cells. α-SMA protein and gene levels were confirmed using Western blot and real time PCR analysis, respectively.

Figure 4:
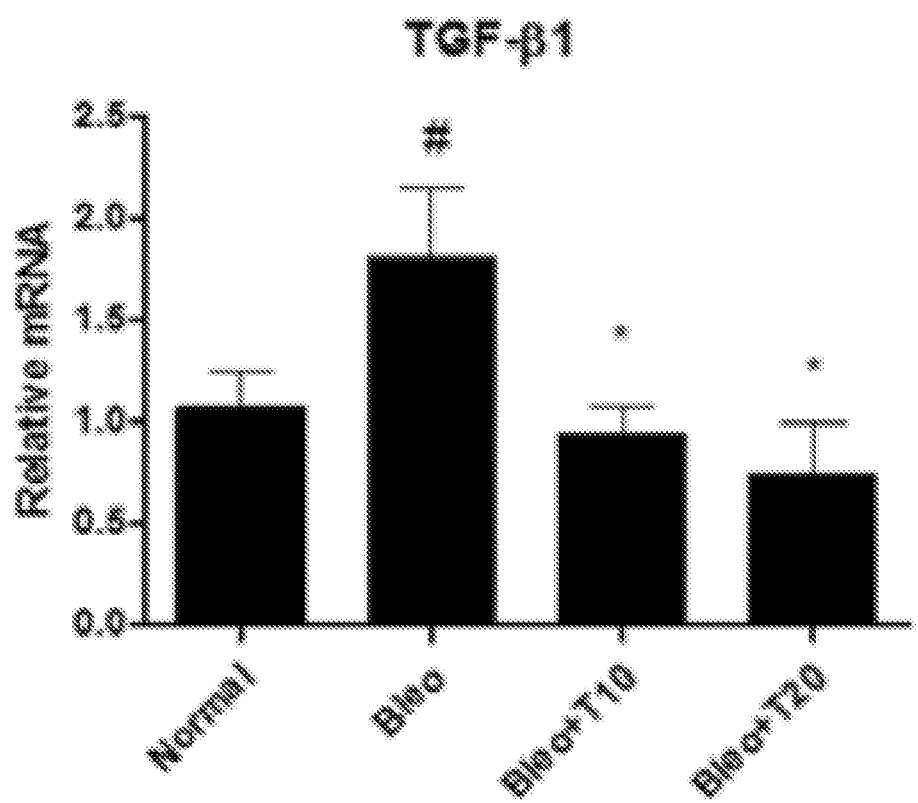
FIG. 4 depicts a bar graph showing transforming growth factor-beta 1 (TGF-β1) mRNA expression in lesional skin, quantified by real-time PCR. TRAIL$_{PEG}$ administration substantially prevented the upregulation of TGF-β1 mRNA; $^{\#}p<0.05$ vs. normal; *p<0.05 vs. vehicle.

Example 4: Effects of TRAIL$_{PEG}$ on Transforming Growth Factor Beta 1 (TGF-β1) and Death Receptor 5 (DR5) Expressions TRAIL$_{PEG}$ Treatment Demonstrated that Skin Scleroderma May be Reversed in In Vivo Models Transforming growth factor is a key mediator of fibrosis in a variety of fibrotic disorders, as well as in animal models of bleomycin-induced fibrosis. To evaluate the modulation of the TGF-β1 by TRAIL$_{PEG}$ in vivo, TGF-β1 mRNA was examined in lesional skin. TRAIL$_{PEG}$ administration substantially prevented the upregulation of TGF-β1 mRNA (FIG. 4).

Example 5: TRAIL$_{PEG}$ Reversed Pulmonary Fibrosis

Figure 5:
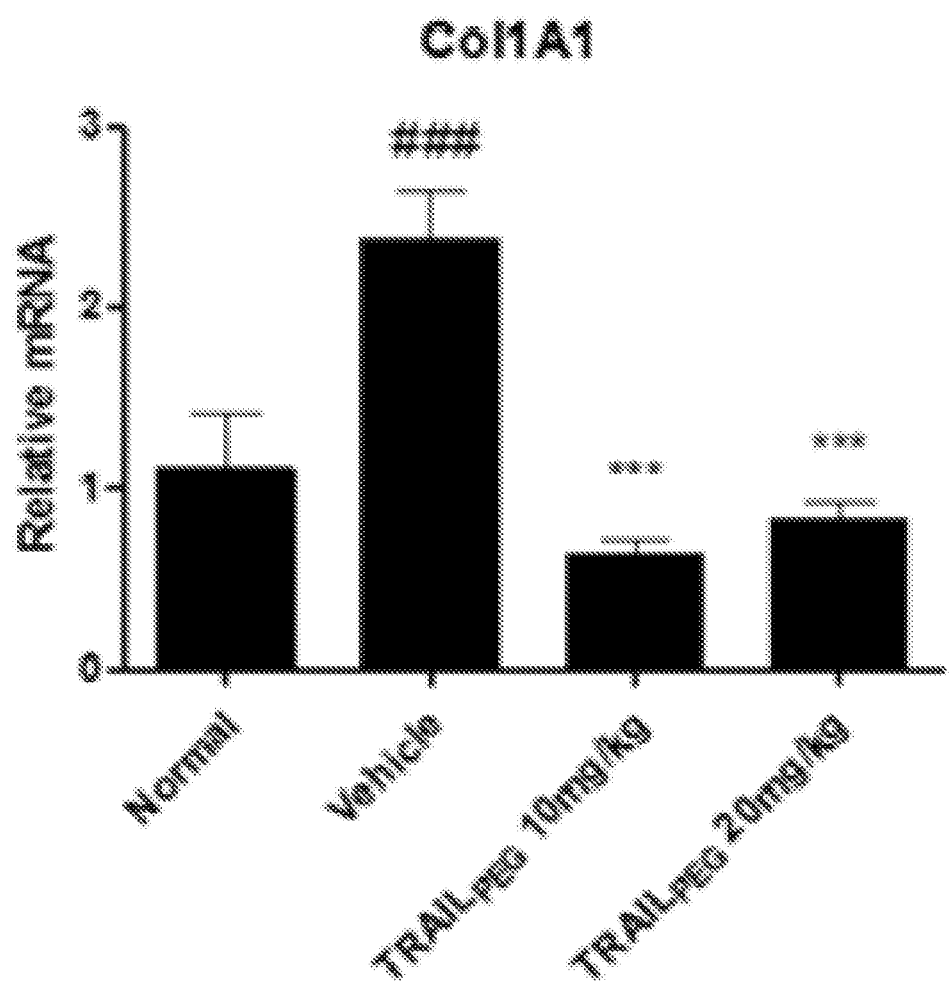
FIG. 5 depicts a bar graph showing Col1A1 mRNA expression in induced lung fibrosis, quantified by real-time PCR. The results showed a greater than 50% increase in the levels of Col1A1 mRNA in mice treated with bleomycin compared with normal mice; $^{\#}p<0.05$, $^{\#\#\#\#}p<0.001$ vs. normal: p<0.01, *p<0.001 vs. vehicle.

TRAIL$_{PEG}$ Treatment Abrogated Collagen and Myofibroblast Stimulation in Pulmonary Fibrosis To examine the effects of TRAIL$_{PEG}$ on collagen and α-SMA expression in bleomycin induced lung fibrosis, mRNA in the lung was quantified by real-time PCR. The results showed a greater than 50% increase in the levels of Col1A1 (FIG. 5) mRNA in mice treated with bleomycin as compared with normal mice. TRAIL$_{PEG}$ treatment markedly attenuated the up-regulation of collagen mRNA.

Figure 6A:
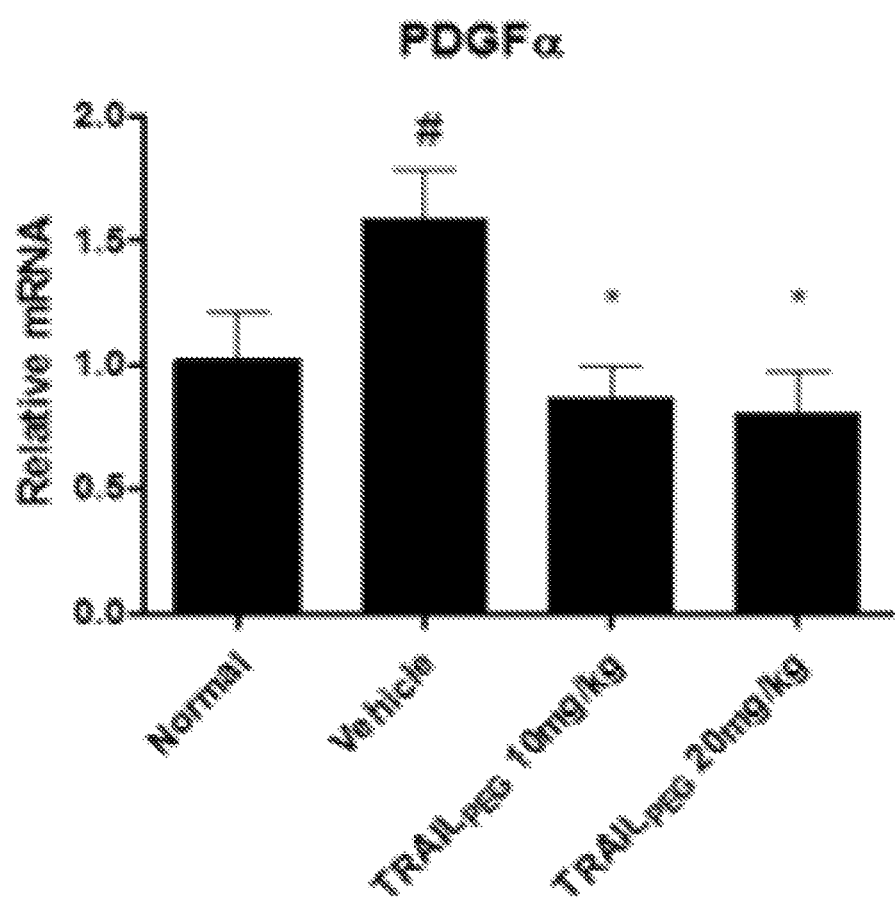
FIG. 6A depicts a bar graph showing platelet-derived growth factor (PDGF)-α mRNA expression in bleomycin induced lung, quantified by real-time PCR. The results showed increase in the levels of PDGFα mRNA in mice treated with bleomycin compared with normal mice. TRAIL$_{PEG}$ treatment markedly attenuated the up-regulation of PDGF-α mRNA; $^{\#}p<0.05$, $^{\#\#\#\#}p<0.001$ vs. normal; *p<0.05, *p<0.001 vs. vehicle.
Figure 6B:
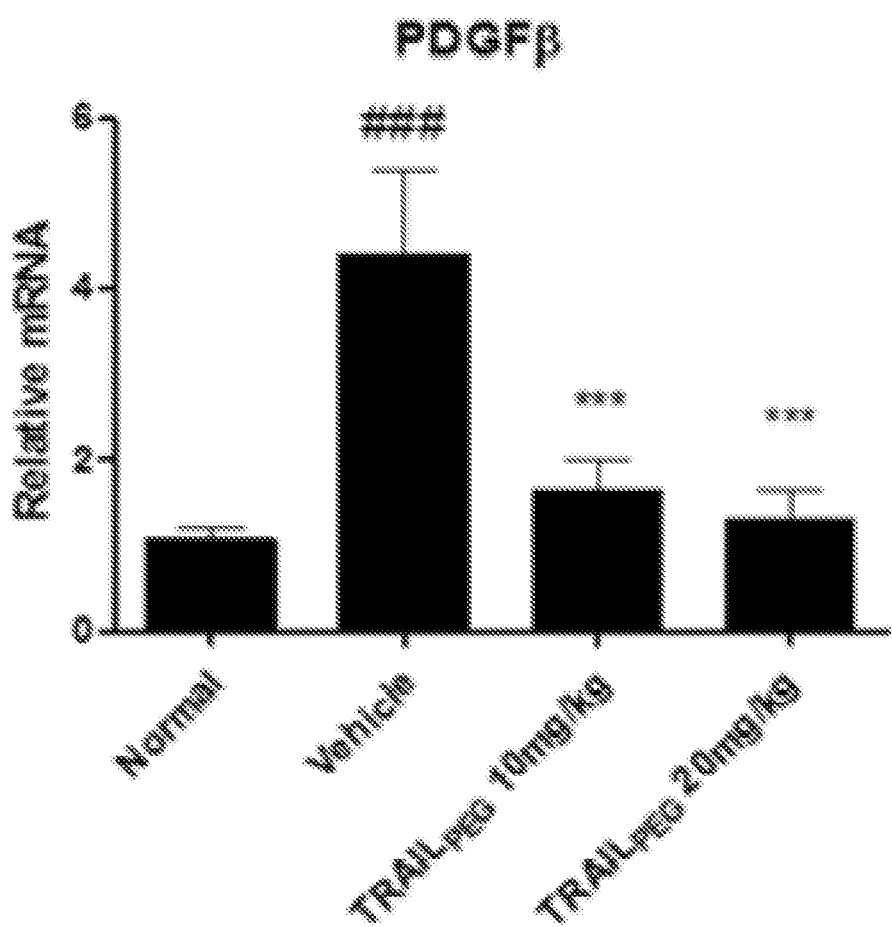
FIG. 6B** depicts a bar graph showing PDGF-β mRNA expression in bleomycin induced lung, quantified by real-time PCR. The results showed increase in the levels of PDGF-β mRNA in mice treated with bleomycin compared with normal mice. TRAIL$_{PEG}$ treatment markedly attenuated the up-regulation of PDGF-β mRNA; $^{\#}p<0.05$, $^{\#\#\#\#}p<0.001$ vs. normal: *p<0.05, ***p<0.001 vs. vehicle.

TRAIL$_{PEG}$ Attenuated Platelet-Derived Growth Factor (PDGFs) in Bleomycin-Induced Pulmonary Fibrosis PDGF plays a key role in expansion of myofibroblasts by stimulating their proliferation migration and survival. Elevated levels of PDGF have been consistently demonstrated in the fibrotic lesions of the lung. To examine the effects of TRAIL$_{PEG}$ treatment on PDGF expression in bleomycin induced lung, mRNA in the lung was quantified by real-time PCR. The results showed increases in the levels of PDGFα (FIG. 6A) and PDGFβ (FIG. 6B) mRNA in mice administered bleomycin, as compared with normal mice. TRAIL$_{PEG}$ treatment markedly attenuated the up-regulation of PDGF mRNA.

Example 6: TRAIL$_{PEG}$ Reversed Advanced Fibrosis in Bleomycin-Induced SSc Mouse Models Study Design II (Advanced Fibrosis in Bleomycin-Induced SSc Mouse Models)

To further confirm antifibrotic efficacy of DR agonists in SSc mouse models of advanced fibrosis, mice (DBA2/J) were treated with subcutaneous (s.c.) bleomycin for three weeks (day 0-21) to establish skin fibrosis and further treated with DR agonists or PBS for additional three weeks. TRAIL$_{PEG}$ (5 mg/kg) or PBS were intraperitoneally (i.p.) administered every other day for three weeks (day 22-42; n=7-10 per group). Tissue samples were collected on Day 43 and analyzed as described above. Hydroxyproline (collagen marker) content was measured by assay kit (Sigma). Also, skin tissue sections were analyzed for a number of fibrogenic markers (collagen, α-SMA) using immunohistochemistry. Tissue homogenates were analyzed by western blot and RT-PCT for DR5, α-SMA, TGF-β1, collagens, PDGFR and PDGF. To confirm TRAIL-induced apoptosis, caspase-8 and caspase-3/7 activity in skin tissues were measured by assay kits.

Results:

Injection of bleomycin induced prominent skin fibrosis with dermal thickening, deposition of collagen, loss of intradermal adipose tissue, dense inflammatory infiltrates and myofibroblast differentiation. Prolonged injection of bleomycin for 6 weeks approximates the severity of skin fibrosis as compared with injections for 3 weeks followed by injection of NaCl for additional 3 weeks. Treatment with TRAIL$_{PEG}$ started after 3 weeks of bleomycin-challenge ameliorated the progression of fibrosis with a significant decrease of inflammatory infiltration, dermal thickness, hydroxyproline content and myofibroblast counts as compared with PBS treated mice injected with bleomycin for 3 weeks (Table 4). Furthermore, TRAIL$_{PEG}$ reduced the expression of fibrotic markers (ACTA2, TGF-β1, Col1A1, Col1A2, PDGFR-β and PDGFα) mRNA levels in pre-established dermal fibrosis samples (Table 5). It was also found that DR5 mRNA levels were significantly higher in bleomycin treated mice compared to PBS treated mice. An increase in TRAIL-induced apoptosis in the skin of TRAIL$_{PEG}$ treated bleomycin induced SSc mice but not in the skin of healthy mice was confirmed (Table 6).

TABLE 4

Effects of TRAIL$_{PEG}$ in belomycin induced skin fibrosis (relative fold).

| | Normal | | Bleomycin | |
| --- | --- | --- | --- | --- |
| | PBS | TRAIL$_{PEG}$ 5 mg/kg | PBS | TRAIL$_{PEG}$ 5 mg/kg |
| Dermal Thickness | 1 ± 0.1 | 1.2 ± 0.1 | 2.7 ± 0.4*** | 1.4 ± 0.4### |
| Hydroxyproline | 1 ± 0.2 | 1.3 ± 0.3 | 2. ± 0.5*** | 1.4 ± 0.5## |
| Myofibroblast counts | 1.0 ± 0.2 | 1.3 ± 0.1 | 3.4 ± 1.2*** | 0.9 ± 0.2### |

***P < 0.001 vs Normal + PBS,
P < 0.01,
P < 0.001 vs Bleomycin + PBS.

TABLE 5

Real time PCR analysis (relative fold) of mRNA levels of DR5, ACTA2, TGF-β1, Col1A1, Col1A2, PDGFR-β and PDGFα in the skin.

| | Normal | | Bleomycin | |
| --- | --- | --- | --- | --- |
| Gene | PBS | TRAIL$_{PEG}$ 5 mg/kg | PBS | TRAIL$_{PEG}$ 5 mg/kg |
| DR5 | 1.1 ± 0.4 | 1.1 ± 0.5 | 3.5 ± 3.4* | 4.3 ± 2.1*** |
| ACTA2 (α-SMA) | 1.1 ± 0.5 | 1.2 ± 0.4 | 4.4 ± 1.7*** | 0.8 ± 0.4### |
| TGF-β1 | 1.2 ± 0.6 | 1.1 ± 0.3 | 2.5 ± 0.7*** | 1.3 ± 0.5### |
| Col1A1 | 1.1 ± 0.6 | 0.8 ± 0.3 | 1.5 ± 0.3*** | 0.2 ± 0.2### |
| Col1A2 | 1.1 ± 0.5 | 1.5 ± 0.5 | 2.8 ± 1.3*** | 0.6 ± 0.7### |
| PDGFRβ | 1.1 ± 0.4 | 0.9 ± 0.1 | 2.1 ± 1.2*** | 1.5 ± 0.8# |
| PDGFα | 1.1 ± 0.4 | 0.9 ± 0.3 | 1.8 ± 0.2*** | 1.0 ± 0.3### |

*P < 0.05,
***P < 0.001 vs Normal + PBS,
P < 0.05,
P < 0.001 vs Bleomycin + PBS.

TABLE 6

Caspase-8 and -3/7 activity in the skin of control groups and bleomycin-induced skin fibrosis mice treated with TRAIL$_{PEG}$

| | Normal | | Bleomycin | |
| --- | --- | --- | --- | --- |
| Activity | PBS | TRAIL$_{PEG}$ 5 mg/kg | PBS | TRAIL$_{PEG}$ 5 mg/kg |
| Caspase-8 | 1.0 ± 0.6 | 1.1 ± 0.5 | 2.1 ± 0.7 | 4.0 ± 1.7* |
| Caspase-3/7 | 1.0 ± 0.6 | 1.3 ± 0.5 | 1.9 ± 0.5 | 4.0 ± 1.8** |

*P < 0.05,
**P < 0.01 vs Normal + PBS.

Example 7: DR Agonist (TRAIL$_{PEG}$) Ameliorates Fibrosis in Tight Skin-1 (TSK-1) Transgenic SSc Mouse Models The effects of DR agonist (TRAIL$_{PEG}$) in TSK-1 mice was investigated. The TSK-1 phenotype is caused by a dominant mutation in the fibrillin-1 gene that leads to an SSc-like disease with minor infiltrates, autoantibody production and fibrosis of the skin. This model mimics the later stages of skin fibrosis with less inflammation. TSK-1 mice were purchased from JAX® Laboratory). Treatment was started at an age 5 weeks and the outcome was investigated at an age of 10 weeks. TRAIL$_{PEG}$ (5 mg/kg) or PBS were intraperitoneally (i.p.) administered every other day in wild type (WT) mice or TSK-1 mice for five weeks (week 5-10; n=7-10 per group). As summarized in Table 7, TSK-1 mice demonstrated increased dermal thickness, hydroxyproline content (collagen marker) and α-SMA+ myofibroblast cell population compared to that of control (wild type, WT). Treatment of TSK-1 mice with TRAIL$_{PEG}$ (1 mg/kg) for 5 weeks reduced hypodermal thickening, hydroxyproline content and myofibroblast counts of the skin as compared with PBS treated TSK-1 mice.

TABLE 7

Effects of TRAIL$_{PEG}$ in TSK-1 mice (relative fold).

|  | WT | TSK-1 | |
| --- | --- | --- | --- |
|  | PBS | PBS | TRAIL$_{PEG}$ 1 mg/kg |
| Dermal Thickness | 1.0 ± 0.5 | 2.7 ± 1.2** | 1.8 ± 0.7# |
| Hydroxyproline | 1.0 ± 0.2 | 1.4 ± 0.2*** | 1.1 ± 0.7### |
| Myofibroblast | 1.0 ± 0.4 | 2.3 ± 1.0* | 1.2 ± 0.6# |

*P < 0.05,
**P < 0.01,
***P < 0.001 vs WT + PBS,
P < 0.05,
P < 0.001 vs TSK-1 + PBS.

Example 8: DR Antibody (MD5-1, Mouse Anti-DR5 Antibody) Reversed Advanced Fibrosis in Bleomycin-Induced SSc Mouse Models To further confirm antifibrotic efficacy of agonistic DR antibody in SSc mouse models of advanced fibrosis, as described in the Study design 11, mice (DBA2/J) were treated with subcutaneous (s.c.) bleomycin for three weeks (day 0-21) to establish skin fibrosis and further treated with DR5 antibody (100 ug per mouse). IgG (control) or PBS every other day for additional three weeks (day 22-42; n=7-10 per group).

Tissue samples were collected on Day 43 and analyzed as described above. Dermal thickness and hydroxyproline (collagen marker) content as well as α-SMA+ myofibroblast cell populations were measured as described above. Tissue homogenates were analyzed by RT-PCT for α-SMA, TGF-β1, collagens, PDGFR and PDGF. To confirm TRAIL-induced apoptosis, caspase-8 and caspase-3/7 activity in skin tissues were measured by assay kits.

Results:

Treatment with Anti-DR5 antibody (MD5-1) for 3 weeks in SSc mouse with pre-established fibrosis ameliorated the skin fibrosis with a significant decrease of dermal thickness, hydroxyproline content and myofibroblast counts (Table 8). In addition, the administration of MD5-1 substantially decreased mRNA level of ACTA2 (α-SMA), Col1A1, Col1A2, TGF-β1, PDGFR-β and PDGFα in pre-established fibrosis (Table 9). DR-mediated apoptosis by MD5-1 through caspase-8 and caspase-3/7 activity assay was confirmed (Table 10).

TABLE 8

Effects of DR agonistic antibody (MD5-1) in bleomycin-induced SSc mice (relative fold).

|  | Normal | Bleomycin | |
| --- | --- | --- | --- |
|  | IgG | IgG | Anti-DR5 Antibody |
| Dermal Thickness | 1.0 ± 0.1 | 2.6 ± 0.5*** | 1.3 ± 0.2### |
| Hydroxyproline | 1.0 ± 0.2 | 1.9 ± 0.7*** | 0.9 ± 0.3### |
| Myofibroblast | 1.0 ± 0.2 | 3.4 ± 1.2*** | 1.3 ± 0.4### |

***P < 0.001 vs Normal + IgG,
P < 0.001 vs Bleomycin + IgG.

TABLE 9

Real time PCR analysis (relative fold) of mRNA levels of ACTA2, TGF-β1, Col1A1, Col1A2, PDGFR-β and PDGFα in the skin.

|  | Normal | Bleomycin | |
| --- | --- | --- | --- |
| Gene | IgG | IgG | Anti-DR5 Antibody |
| ACTA2 | 1.0 ± 0.3 | 3.1 ± 0.8*** | 0.6 ± 0.3### |
| TGF-β1 | 1.0 ± 0.2 | 1.3 ± 0.2*** | 0.3 ± 0.1### |
| Col1A1 | 1.0 ± 0.4 | 2.7 ± 1.5** | 0.1 ± 0.1### |
| Col1A2 | 1.0 ± 0.2 | 1.8 ± 0.7*** | 0.2 ± 0.1### |
| PDGFRβ | 1.0 ± 0.2 | 1.9 ± 1.1* | 0.4 ± 0.1### |
| PDGFα | 1.0 ± 0.2 | 2.0 ± 0.5*** | 1.0 ± 0.4### |

*P < 0.05,
***P < 0.001 vs Normal + IgG,
P < 0.001 vs Bleomycin + IgG.

TABLE 10

Caspase-8 and -3/7 activity in the skin of control groups and bleomycin-induced skin fibrosis mice treated with DR antibody.

|  | Normal | Bleomycin | |
| --- | --- | --- | --- |
| Activity | IgG | IgG | Anti-DR5 |
| Caspase-8 | 1.0 ± 0.5 | 2.4 ± 0.9 | 3.5 ± 1.2*** |
| Caspase-3/7 | 1.0 ± 0.5 | 1.7 ± 0.4 | 2.6 ± 1.1** |

**P < 0.01,
***P < 0.001 vs Normal + IgG.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

EQUIVALENTS

Those skilled in the art will recognize, or be able to ascertain using no more than routine experimentation, many equivalents to the specific embodiments described herein. Such equivalents are intended to be encompassed by the following claims.

What is claimed is:

1. A method for treating systemic sclerosis (SSc) in a mammalian subject, the method comprising:
administering to the subject in need thereof a death receptor 4 (DR4) or DR5 agonist in an amount effective to block activation of fibroblasts or deplete activated myofibroblasts induced by transforming growth factor (TGF)-beta, and reduce collagen deposition to normal levels.

2. The method of claim 1, wherein the SSc is limited scleroderma or diffuse scleroderma.

3. The method of claim 1, wherein the death receptor agonist comprises a tumor necrosis factor (TNF)-related apoptosis-inducing ligand (TRAIL), a TRAIL analogue, a death receptor agonistic antibody, or a derivative thereof.

4. The method of claim 1, wherein the death receptor agonist comprises human recombinant TRAIL, a human TRAIL analogue, or a derivative thereof.

5. The method of claim 1, wherein the death receptor agonist comprises native TRAIL, a native TRAIL analogue, or a derivative thereof.

6. The method of claim 1, wherein the death receptor agonist comprises a DR5 agonist selected from the group consisting of Lexatumumab, Tigatuzumab, Conatumumab, Drozitumab, HGSTR2J/KMTRS, and LBY-135.

7. The method of claim 1, wherein the death receptor agonist comprises a multivalent DR agonist selected from the group consisting of TAS266 and scTRAIL-RBDs.

8. The method of claim 1, wherein the death receptor agonist comprises human recombinant TRAIL, a human TRAIL analogue, or a derivative thereof selectively attached at its N-terminus to a polymer.

9. The method of claim 8, wherein the polymer comprises polyethylene glycol (PEG), or derivative thereof.

10. The method of claim 9, wherein the PEG or PEG derivative is selected from the group consisting of methoxypolyethylene glycol succinimidyl propionate, methoxypolyethylene glycol succinate N-hydroxysuccinimide, methoxypolyethylene glycol propionaldehyde, methoxypolyethylene glycol maleimide, and multiple-branched polyethylene glycol.

11. The method of claim 9, wherein the PEG or derivative thereof has a molecular weight of between 1,000 Da and 100,000 Da.

12. The method of claim 9, wherein the PEG or derivative thereof has a molecular weight of between 5,000 Da and 50,000 Da.

13. The method of claim 1, wherein the death receptor agonist is administered systemically.

14. The method of claim 1, wherein the death receptor agonist is administered locally.

15. The method of claim 1, wherein the death receptor agonist is administered subcutaneously.

16. The method of claim 1, wherein the fibrosis is treated or prevented in the subject, as compared to an appropriate control.

17. The method of claim 1, wherein the death receptor agonist is administered by injection at a dosage of between 0.001 mg/kg and 50 mg/kg to the subject.

18. The method of claim 1, wherein the death receptor agonist is administered by injection at a dosage of between 0.5 mg/kg and 50 mg/kg to the subject.

19. The method of claim 1, wherein the effective amount of the death receptor agonist is administered to the subject over a period of one or more days.

20. The method of claim 1, wherein the subject is human.

21. The method of claim 1, wherein the administering of the effective amount of a death receptor agonist reduces dermal thickness, skin collagen levels, TGF-$\beta$, PDGFR, PDGF, IL-6 levels, and/or reduces $\alpha$-SMA$^+$ fibroblastic cells as compared to an appropriate control.

22. The method of claim 21, wherein the effective amount of the death receptor agonist is administered in one or more dosages.

23. The method of claim 1, wherein the death receptor agonist is in an effective amount to reduce dermal thickness to normal levels.

24. The method of claim 1, wherein the administering of the effective amount of a death receptor agonist restores normal wound healing of the skin.

* * * * *

UNITED STATES PATENT AND TRADEMARK OFFICE
CERTIFICATE OF CORRECTION

PATENT NO. : 11,007,251 B2  
APPLICATION NO. : 16/063592  
DATED : May 18, 2021  
INVENTOR(S) : Seulki Lee et al.

Page 1 of 1

It is certified that error appears in the above-identified patent and that said Letters Patent is hereby corrected as shown below:

In the Specification

Column 7, Line 58, please replace the term "treat." with "treat,".
Column 7, Line 66, please replace the term "prevention." with "prevention,".
Column 8, Line 14, please replace the term "0.05%." with "0.05%,".
Column 12, Line 16, please replace the term "DR-S-selective" with "DR-5-selective".
Column 12, Line 18, please replace the term "D269H/E 95R" with "D269H/E195R".
Column 13, Line 54, please replace the term "6.000" with "6,000".
Column 21, Line 27, please replace the term "instances." with "instances,".
Column 24, Line 48, please replace the term "foxod" with "food".
Column 29, Line 16, please replace the term "Lime" with "time".

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 1

<210> SEQ ID NO 1
<211> LENGTH: 281
<212> TYPE: PRT
<213> ORGANISM: Homo sapiens

<400> SEQUENCE: 1

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
            165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280
```